(12) United States Patent
Kapeller-Libermann

(10) Patent No.: US 6,329,171 B1
(45) Date of Patent: Dec. 11, 2001

(54) 23484, A NOVEL HUMAN UBIQUITIN PROTEASE

(75) Inventor: Rosana Kapeller-Libermann, Chestnut Hill, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/408,865

(22) Filed: Sep. 30, 1999

(51) Int. Cl.[7] .......................... C12N 15/12; C12N 15/63; C12N 15/85; C07H 21/00
(52) U.S. Cl. .................. 435/69.1; 435/252.3; 435/325; 435/455; 435/471; 536/23.1; 536/23.5
(58) Field of Search ............................... 800/8; 435/183, 435/320.1, 325; 424/130.1; 530/350; 514/44; 536/23.1, 23.5

(56) References Cited

FOREIGN PATENT DOCUMENTS

| WO00/01817 | 1/2000 | (WO) . |
| WO00/58473A2 | 10/2000 | (WO) . |

OTHER PUBLICATIONS

Henchoz et al. Molecular and cellular biology 16(10):5717–5725, Oct. 1996.*
Hershko et al. Annual Review in Biochemistry 67:425–479, 1998.*
Wall et al. Journal of Dary Science 80:2213–2224, 1997.*
Hammer et al. Journal of Animal Science 63:269–278, 1986.*
Verma et al. Nature 389:239–242, Sep. 1997.*
Anderson, W. Nature 392:25–30, Apr. 1998.*
D'Andrea et al. (1998) "Deubiquitinating Enzymes: A New Class of Biological Regulators" *Critical Reviews in Biochemistry and Molecular Biology* 33(5):337–352. (XP–000943127).
EMBL Database Accession No. AK001671. (XP–002159104).
Nagase et al. (2000) "Prediction of the Coding Sequences of Unidentified Human Genes, XVII. The Complete Sequences of 100 New cDNA Clones from Brain Which Code for Large Proteins *in vitro*" *DNA Research* 7:143–150. (XP–000943428).
PCT Notification of Transmittal of the International Search Report or the Declaration mailed Feb. 8, 2001, International Application No. PCT/US00/26915, International Filing Date Sep. 29, 2000.
Blast Search in Patent, NRP, DBEST, and NRN Databases.
Blast Search of 23431 against Dbest, NRN, NRP and Patent Databases.
GenBank Report, Accession No. AC004895, Waterston, R.H., "The Sequence of Homo Sapiens Clone," Unpublished, Waterston, R. H., Direct Submission, Submitted May 29, 1999.
Zhu et al, DUB–2 is a Member of a Novel Family of Cytokine–Inducible Deubiquitinating Enzymes, *J. Biol. Chem*, Jan. 1997, pp. 51–57, vol. 272(1), published Medical Abstract.
Jensen et al., BAP1: A Novel Ubiquitin Hydrolase Which Binds to the BRCA1 Ring Finger and Enhances BRCA1–Mediated Cell Growth Suppression, Oncogen, Mar. 5, 1998, pp. 1097–1112, vol. 16(9), Published Medical Abstract.
Lucero et al., Catabolite Inactivation of the Yeast Maltose Transporter Requires Ubiquitin–ligase npi 1/rsp5 and Ubiquitin–Hydrolase npi2/doa4, FEMS Microbiology Letters, Feb. 15, 1997, pp. 273–277, vol. 147(2), Published Medical Abstract.
Swanson et al., a Ubiquitin C–Terminal Hydrolase Gene on the Proximal Short Arm of the X Chromosome: Implications for X–Linked Retinal Disorders, Human Molecular Genetics, Apr. 1996, pp. 533–538, vol. 5(4), Published Medical Abstract.
Zhu et al. (1997), "DUB–2 Is a Member of a Novel Family of Cytokine–inducible Deubiquitinating Enzymes," *The Journal of Biological Chemistry* 272(1):51–57, Division of Pediatric Oncology and Division of Cellular and Molecular Biology.
Jensen et al. (1998), "BAP1: A Novel Ubiquitin Hydrolase Which Binds to the BRCA1Ring Finger and Enhances BRCA1 Mediated Cell Growth Suppression," *Oncogene* 16:1097–1112, The Wistar Institute.
Lucero et al. (1997), "Catabolite Inactivation of the Yeast Maltose Transporter Requires Ubiquitin–Ligase npi1/rsp5 and Ubiquitin–Hydrolase npi2/doa4," *FEMS Microbiology Letters* 147:273–277, Federation of European Microbiological Societies.
Swanson et al. (1996), "A Ubiquitin C–terminal Hydrolase Gene on the Proximal Short Arm of the X Chromosome: Implications for X–linked Retinal Disorders," *Human Molecular Genetics* 5(4):533–538, Howard Hughes Medical Institute.

* cited by examiner

*Primary Examiner*—Karen M. Hauda
*Assistant Examiner*—Joseph T. Woitach
(74) *Attorney, Agent, or Firm*—Alston & Bird LLP

(57) ABSTRACT

The present invention relates to a newly identified human ubiquitin protease belonging to the family of mammalian deubiquitinating enzymes. The invention also relates to polynucleotides encoding the ubiquitin protease. The invention further relates to methods using the ubiquitin protease polypeptides and polynucleotides as a target for diagnosis and treatment in ubiquitin-mediated or -related disorders. The invention further relates to drug-screening methods using the ubiquitin protease polypeptides and polynucleotides to identify agonists and antagonists for diagnosis and treatment. The invention further encompasses agonists and antagonists based on the ubiquitin protease polypeptides and polynucleotides. The invention further relates to procedures for producing the ubiquitin protease polypeptides and polynucleotides.

18 Claims, 12 Drawing Sheets

Input file Fbb23484FL2.seq; Output File 23484.trans
Sequence length 3941

CACGCGTCCGGGCGCCGGAGGCCCGGATGGTGCGCGTGCTGGGCCGCGGGCCGAAGGAGTCGCCAGGGCTGCGTAGGCT

TGTGGCGCGCCCGCGGAGAGGCCGGGGCTCTGACGCCCGCTCTGCGGCTTCGGTGTTTGAACAGGCCACAGTCCAGGAG

CGCTTACATTCAGGAGCTCCGCGTAGCACCTGCCCAACCAAACTCAGCCCTCCGTTAAGATCCTGGTTCCATGCCGCAG

| | | | | | | | | M | P | I | V | D | K | L | K | E | | 9 |
|---|---|---|---|---|---|---|---|---|---|---|---|---|---|---|---|---|---|---|
| TAGGACAGCAGGCCCAAGTCTGCACATCCCAGTGATGCACC | | | | | | | | ATG | CCA | ATA | GTG | GAT | AAG | TTG | AAG | GAG | | 27 |
| A | L | K | P | G | R | K | D | S | A | D | D | G | E | L | G | K | L | L | A | | 29 |
| GCC | CTG | AAA | CCC | GGC | CGC | AAG | GAC | TCG | GCT | GAT | GAT | GGA | GAA | CTG | GGG | AAG | CTT | CTT | GCC | | 87 |
| S | S | A | K | K | V | L | L | Q | K | I | E | F | E | P | A | S | K | S | F | | 49 |
| TCC | TCT | GCC | AAG | AAG | GTC | CTT | TTA | CAG | AAA | ATC | GAG | TTC | GAG | CCA | GCC | AGC | AAG | AGC | TTC | | 147 |
| S | Y | Q | L | E | A | L | K | S | K | Y | V | L | L | N | P | K | T | E | G | | 69 |
| TCC | TAC | CAG | CTG | GAG | GCC | TTA | AAG | AGC | AAA | TAT | GTG | TTG | CTC | AAC | CCC | AAA | ACA | GAG | GGA | | 207 |
| A | S | R | H | K | S | G | D | D | P | P | A | R | R | Q | G | S | E | H | T | | 89 |
| GCT | AGT | CGC | CAC | AAG | AGT | GGA | GAT | GAC | CCA | CCG | GCC | AGG | AGA | CAG | GGC | AGT | GAG | CAC | ACG | | 267 |
| Y | E | S | C | G | D | G | V | P | A | P | Q | K | V | L | F | P | T | E | R | | 109 |
| TAT | GAG | AGC | TGT | GGT | GAC | GGA | GTC | CCA | GCC | CCG | CAG | AAA | GTG | CTT | TTC | CCC | ACG | GAG | CGA | | 327 |
| L | S | L | R | W | E | R | V | F | R | V | G | A | G | L | H | N | L | G | N | | 129 |
| CTG | TCT | CTG | AGG | TGG | GAG | CGG | GTC | TTC | CGC | GTG | GGC | GCA | GGA | CTC | CAC | AAC | CTT | GGC | AAC | | 387 |
| T | C | F | L | N | A | T | I | Q | C | L | T | Y | T | P | P | L | A | N | Y | | 149 |
| ACC | TGC | TTT | CTC | AAT | GCC | ACC | ATC | CAG | TGC | TTG | ACC | TAC | ACA | CCA | CCT | CTA | GCC | AAC | TAC | | 447 |
| L | L | S | K | E | H | A | R | S | C | H | Q | G | S | F | C | M | L | C | V | | 169 |
| CTG | CTC | TCC | AAG | GAG | CAT | GCT | CGC | AGC | TGC | CAC | CAG | GGA | AGC | TTC | TGC | ATG | CTG | TGT | GTC | | 507 |
| M | Q | N | H | I | V | Q | A | F | A | N | S | G | N | A | I | K | P | V | S | | 189 |
| ATG | CAG | AAC | CAC | ATT | GTC | CAG | GCC | TTC | GCC | AAC | AGC | GGC | AAC | GCC | ATC | AAG | CCC | GTC | TCC | | 567 |
| F | I | R | D | L | K | K | I | A | R | H | F | R | F | G | N | Q | E | D | A | | 209 |
| TTC | ATC | CGA | GAC | CTG | AAA | AAG | ATC | GCC | CGA | CAC | TTC | CGC | TTT | GGG | AAC | CAG | GAG | GAC | GCG | | 627 |
| H | E | F | L | R | Y | T | I | D | A | M | Q | K | A | C | L | N | G | C | A | | 229 |
| CAT | GAG | TTC | CTG | CGG | TAC | ACC | ATC | GAC | GCC | ATG | CAG | AAA | GCC | TGC | CTG | AAT | GGC | TGT | GCC | | 687 |
| K | L | D | R | Q | T | Q | A | T | T | L | V | H | Q | I | F | G | G | Y | L | | 249 |
| AAG | TTG | GAT | CGT | CAA | ACG | CAG | GCT | ACT | ACC | TTG | GTC | CAT | CAA | ATT | TTT | GGA | GGG | TAT | CTC | | 747 |
| R | S | R | V | K | C | S | V | C | K | S | V | S | D | T | Y | D | P | Y | L | | 269 |
| AGA | TCA | CGC | GTG | AAG | TGC | TCC | GTG | TGC | AAG | AGC | GTC | TCG | GAC | ACC | TAC | GAC | CCC | TAC | TTG | | 807 |

FIG. 1A.

```
  D   V   A   L   E   I   R   Q   A   A   N   I   V   R   A   L   E   L   F   V    289
GAC GTC GCG CTG GAG ATC CGG CAA GCT GCG AAT ATT GTG CGT GCT CTG GAA CTT TTT GTG    867
  K   A   D   V   L   S   G   E   N   A   Y   M   C   A   K   C   K   K   K   V    309
AAA GCA GAT GTC CTG AGT GGA GAG AAT GCC TAC ATG TGT GCT AAA TGC AAG AAG AAG GTT    927
  P   A   S   K   R   F   T   I   H   R   T   S   N   V   L   T   L   S   L   K    329
CCA GCC AGC AAG CGC TTC ACC ATC CAC AGA ACA TCC AAC GTC TTA ACC CTT TCC CTC AAG    987
  R   F   A   N   F   S   G   G   K   I   T   K   D   V   G   Y   P   E   F   L    349
CGC TTT GCC AAC TTC AGC GGG GGG AAG ATC ACC AAG GAT GTA GGC TAT CCG GAA TTC CTC   1047
  N   I   R   P   Y   M   S   Q   N   N   G   D   P   V   M   Y   G   L   Y   A    369
AAC ATA CGT CCG TAT ATG TCC CAG AAT AAT GGT GAT CCT GTC ATG TAT GGA CTC TAT GCT   1107
  V   L   V   H   S   G   Y   S   C   H   A   G   H   Y   Y   C   Y   V   K   A    389
GTC CTG GTG CAC TCG GGC TAC AGC TGC CAT GCC GGG CAC TAT TAC TGC TAC GTG AAG GCA   1167
  S   N   G   Q   W   Y   Q   M   N   D   S   L   V   H   S   S   N   V   K   V    409
AGC AAT GGA CAG TGG TAC CAG ATG AAT GAT TCC TTG GTC CAT TCC AGC AAC GTC AAG GTG   1227
  V   L   N   Q   Q   A   Y   V   L   F   Y   L   R   I   P   G   S   K   K   S    429
GTT CTG AAC CAG CAG GCC TAC GTG CTG TTC TAT CTG CGA ATT CCA GGC TCT AAG AAA AGT   1287
  P   E   G   L   I   S   R   T   G   S   S   S   L   P   G   R   P   S   V   I    449
CCC GAG GGC CTC ATC TCC AGG ACA GGC TCC TCC TCC CTT CCC GGC CGC CCG AGT GTG ATT   1347
  P   D   H   S   K   K   N   I   G   N   G   I   I   S   S   P   L   T   G   K    469
CCA GAT CAC TCC AAG AAG AAC ATC GGC AAT GGG ATT ATT TCC TCC CCA CTG ACT GGA AAG   1407
  R   Q   D   S   G   T   M   K   K   P   H   T   T   E   E   I   G   V   P   I    489
CGA CAA GAC TCT GGG ACG ATG AAG AAG CCG CAC ACC ACT GAA GAG ATT GGT GTG CCC ATA   1467
  S   R   N   G   S   T   L   G   L   K   S   Q   N   G   C   I   P   P   K   L    509
TCC AGG AAT GGC TCC ACC CTG GGC CTG AAG TCC CAG AAC GGC TGC ATT CCT CCA AAG CTG   1527
  P   S   G   S   P   S   P   K   L   S   Q   T   P   T   H   M   P   T   I   L    529
CCC TCG GGG TCC CCT TCC CCC AAA CTC TCC CAG ACA CCC ACA CAC ATG CCA ACC ATC CTA   1587
  D   D   P   G   K   K   V   K   K   P   A   P   P   Q   H   F   S   P   R   T    549
GAC GAC CCT GGA AAG AAG GTG AAG AAG CCA GCT CCT CCA CAG CAC TTT TCC CCC AGA ACT   1647
  A   Q   G   L   P   G   T   S   N   S   N   S   S   R   S   G   S   Q   R   Q    569
GCT CAG GGG CTG CCT GGG ACC AGC AAC TCG AAT AGC AGC AGA TCT GGG AGC CAA AGG CAG   1707
  G   S   W   D   S   R   D   V   V   L   S   T   S   P   K   L   L   A   T   A    589
GGC TCC TGG GAC AGC AGG GAT GTT GTC CTC TCT ACC TCA CCT AAG CTC CTG GCT ACA GCC   1767
  T   A   N   G   H   G   L   K   G   N   D   E   S   A   G   L   D   R   R   G    609
ACT GCC AAC GGG CAT GGG CTG AAG GGG AAC GAC GAG AGC GCT GGC CTC GAC AGG AGG GGC   1827
  S   S   S   S   S   P   E   H   S   A   S   S   D   S   T   K   A   P   Q   T    629
TCC AGC AGC TCC AGC CCA GAG CAC TCG GCC AGC AGC GAC TCC ACC AAG GCC CCC CAG ACC   1887
```

FIG. 1B.

```
  P   R   S   G   A   A   H   L   C   D   S   Q   E   T   N   C   S   T   A   G    649
CCC AGG AGT GGA GCG GCC CAT CTC TGC GAT TCT CAG GAA ACG AAC TGT TCC ACC GCT GGC  1947
  H   S   K   T   P   P   S   G   A   D   S   K   T   V   K   L   K   S   P   V    669
CAC TCC AAA ACG CCG CCA AGT GGA GCA GAT TCT AAG ACG GTG AAG CTG AAG TCC CCT GTC  2007
  L   S   N   T   T   T   E   P   A   S   T   M   S   P   P   P   A   K   K   L    689
CTG AGC AAC ACC ACC ACT GAG CCT GCA AGC ACC ATG TCT CCT CCA CCA GCC AAA AAA CTG  2067
  A   L   S   A   K   K   A   S   T   L   W   R   A   T   G   N   D   L   R   P    709
GCC CTT TCT GCC AAG AAG GCC AGC ACC CTG TGG AGG GCG ACC GGC AAT GAC CTC CGT CCA  2127
  P   P   P   S   P   S   S   D   L   T   H   P   M   K   T   S   H   P   V   V    729
CCT CCC CCC TCA CCA TCC TCC GAC CTC ACC CAC CCC ATG AAA ACC TCT CAC CCC GTC GTT  2187
  A   S   T   W   P   V   H   R   A   R   A   V   S   P   A   P   Q   S   S   S    749
GCC TCC ACT TGG CCC GTC CAT AGA GCC AGG GCT GTG TCA CCT GCT CCC CAA TCA TCC AGC  2247
  R   L   Q   P   P   F   S   P   H   P   T   L   L   S   T   P   K   P   P        769
CGC CTG CAA CCC CCC TTC AGC CCC CAC CCC ACA TTG CTG TCC AGT ACC CCC AAG CCC CCA  2307
  G   T   S   E   P   R   S   C   S   S   I   S   T   A   L   P   Q   V   N   E    789
GGG ACG TCA GAA CCA CGG AGC TGC TCC TCC ATC TCG ACG GCG CTG CCT CAG GTC AAC GAG  2367
  D   L   V   S   L   P   H   Q   L   P   E   A   S   E   P   P   Q   S   P   S    809
GAC CTT GTG TCT CTT CCA CAC CAG TTG CCA GAG GCC AGT GAG CCC CCC CAG AGC CCC TCT  2427
  E   K   R   K   K   T   F   V   G   E   P   Q   R   L   G   S   E   T   R   L    829
GAG AAG AGG AAA AAG ACC TTT GTG GGA GAG CCG CAG AGG CTG GGC TCA GAG ACG CGC CTC  2487
  P   Q   H   I   R   E   A   T   A   A   P   H   G   K   R   K   R   K   K   K    849
CCA CAG CAC ATC AGG GAG GCC ACT GCG GCT CCC CAC GGG AAG AGG AAG AGG AAG AAG AAG  2547
  K   R   P   E   D   T   A   A   S   A   L   Q   E   G   Q   T   Q   R   Q   P    869
AAG CGC CCG GAG GAC ACA GCT GCC AGC GCC CTG CAG GAG GGG CAG ACA CAG AGA CAG CCT  2607
  G   S   P   M   Y   R   R   E   G   Q   A   Q   L   P   A   V   R   R   Q   E    889
GGG AGC CCC ATG TAC AGG AGG GAG GGC CAG GCA CAG CTG CCC GCT GTC AGA CGG CAG GAA  2667
  D   G   T   Q   P   Q   V   N   G   Q   Q   V   G   C   V   T   D   G   H   H    909
GAT GGC ACA CAG CCA CAG GTG AAT GGC CAG CAG GTG GGA TGT GTT ACG GAC GGC CAC CAC  2727
  A   S   S   R   K   R   R   R   K   G   A   E   G   L   G   E   E   G   G   L    929
GCG AGC AGC AGG AAG CGG AGG AGG AAA GGA GCA GAA GGT CTT GGT GAA GAA GGC GGC CTG  2787
  H   Q   D   P   L   R   H   S   C   S   P   M   G   D   G   D   P   E   A   M    949
CAC CAG GAC CCA CTT CGG CAC AGC TGC TCT CCC ATG GGT GAT GGT GAT CCA GAG GCC ATG  2847
  E   E   S   P   R   K   K   K   K   K   R   K   Q   E   T   Q   R   A   V        969
GAA GAG TCT CCA AGG AAA AAG AAA AAG AAA AAA AGA AAG CAG GAG ACA CAG CGG GCA GTA  2907
  E   E   D   G   H   L   K   C   P   R   S   A   K   P   Q   D   A   V   V   P    989
GAA GAG GAT GGG CAT CTC AAA TGC CCA AGG AGT GCC AAG CCC CAA GAT GCT GTT GTC CCC  2967
```

FIG. 1C.

```
E   S   S   S   C   A   P   S   A   N   G   W   C   P   G   D   R   M   G   L    1009
GAG TCC AGC AGC TGC GCA CCA TCC GCG AAT GGC TGG TGT CCT GGG GAC CGC ATG GGG CTG  3027
S   Q   A   P   P   V   S   W   N   G   E   R   E   S   D   V   V   Q   E   L    1029
AGC CAG GCC CCT CCT GTG TCT TGG AAT GGA GAG CGG GAG TCT GAT GTG GTC CAG GAA CTG  3087
L   K   Y   S   S   D   K   A   Y   G   R   K   V   L   T   W   D   G   K   M    1049
CTC AAA TAC TCA TCT GAT AAA GCT TAC GGG AGA AAA GTT CTG ACC TGG GAT GGC AAG ATG  3147
S   A   V   S   Q   D   A   I   E   D   S   R   Q   A   R   T   E   T   V   V    1069
TCG GCG GTC AGT CAG GAT GCT ATT GAA GAC AGC AGA CAG GCC CGG ACT GAG ACC GTG GTT  3207
D   D   W   D   E   E   F   D   R   G   K   E   K   K   I   K   K   F   K   R    1089
GAT GAC TGG GAC GAA GAG TTT GAC CGA GGG AAG GAA AAG AAA ATT AAA AAA TTT AAG AGA  3267
E   K   R   R   N   F   N   A   F   Q   K   L   Q   T   R   R   N   F   W   S    1109
GAG AAG AGG AGA AAC TTC AAC GCC TTC CAG AAA CTT CAG ACT CGA CGG AAC TTC TGG TCT  3327
V   T   H   P   A   K   A   A   S   L   S   Y   R   R   *                        1124
GTG ACT CAC CCA GCA AAG GCT GCC AGC CTC AGC TAT CGC CGC TGA                      3372
```

CTGTGCCCCTGTGGAAGGAGATGATCAAGCGGTGCTGATTCACGAGAGTGGAAGCCTCCAGAGCTTGGGGCTTTCTGGC

TGCTCTTCATTGACCTGTGTGTTCCCAGCACACGAACAGCGCCCCTAACGGAGATTTGTTCAGCGACTGAATATACACC

TGTAAACGAGTAGCATGTATACATTGATTTTGATTACAAATGGTTCTGTATTATATACCACCGTTCTGACTGCTTTTTT

CACTTATAGCTTGGAAATTGTCTTCTGTTGGTAATACAGAAATCTGTTTCAGTC

FIG. 1D.

Prosite Pattern Matches for 23484

Prosite version: Release 12.2 of February 1995

>PS00001|PDOC00001|ASN_GLYCOSYLATION N-glycosylation site.

| Query: | 134 | NATI | 137 |
|---|---|---|---|
| Query: | 333 | NFSG | 336 |
| Query: | 398 | NDSL | 401 |
| Query: | 492 | NGST | 495 |
| Query: | 560 | NSSR | 563 |

FIG. 4A.

| Query: | 644 | NCST | 647 |
| Query: | 672 | NTTT | 675 |

>PS00004|PD0C00004|CAMP_PHOSPHO_SITE cAMP- and cGMP-dependent protein kinase phosphorylation site.

| Query: | 15  | RKDS | 18  |
| Query: | 313 | KRFT | 316 |
| Query: | 607 | RRGS | 610 |
| Query: | 694 | KKAS | 697 |
| Query: | 812 | RKKT | 815 |

>PS00005|PD0C00005|PKC_PHOSPHO_SITE Protein kinase C phosphorylation site.

| Query: | 31  | SAK | 33  |
| Query: | 107 | TER | 109 |
| Query: | 111 | SLR | 113 |
| Query: | 312 | SKR | 314 |
| Query: | 327 | SLK | 329 |
| Query: | 426 | SKK | 428 |
| Query: | 453 | SKK | 455 |
| Query: | 467 | TGK | 469 |
| Query: | 475 | TMK | 477 |
| Query: | 515 | SPK | 517 |
| Query: | 546 | SPR | 548 |
| Query: | 561 | SSR | 563 |
| Query: | 566 | SQR | 568 |
| Query: | 582 | SPK | 584 |
| Query: | 623 | STK | 625 |
| Query: | 629 | TPR | 631 |
| Query: | 662 | TVK | 664 |

FIG. 4B.

| Query: | 692 | SAK | 694 |
| Query: | 748 | SSR | 750 |
| Query: | 765 | TPK | 767 |
| Query: | 809 | SEK | 811 |
| Query: | 865 | TQR | 867 |
| Query: | 911 | SSR | 913 |
| Query: | 952 | SPR | 954 |
| Query: | 965 | TQR | 967 |
| Query: | 980 | SAK | 982 |
| Query: | 1034 | SDK | 1036 |
| Query: | 1103 | TRR | 1105 |
| Query: | 1120 | SYR | 1122 |

>PS00006|PDOC00006|CK2_PHOSPHO_SITE Casein kinase II phosphorylation site.

| Query: | 18 | SADD | 21 |
| Query: | 75 | SGDD | 78 |
| Query: | 92 | SCGD | 95 |
| Query: | 260 | SVSD | 263 |
| Query: | 481 | TTEE | 484 |
| Query: | 527 | TILD | 530 |
| Query: | 613 | SSPE | 616 |
| Query: | 656 | SGAD | 659 |
| Query: | 673 | TTTE | 676 |
| Query: | 703 | TGND | 706 |
| Query: | 807 | SPSE | 810 |
| Query: | 1067 | TVVD | 1070 |

FIG. 4C.

>PS00007|PDOC00007|TYR_PHOSPHO_SITE Tyrosine kinase phosphorylation site.

| | | | |
|---|---|---|---|
| Query: | 83 | RQGSEHTY | 90 |
| Query: | 338 | KITKDVGY | 345 |
| Query: | 1031 | KYSSDKAY | 1038 |

>PS00008|PDOC00008|MYRISTYL N-myristoylation site.

| | | | |
|---|---|---|---|
| Query: | 85 | GSEHTY | 90 |
| Query: | 336 | GGKITK | 341 |
| Query: | 486 | GVPISR | 491 |
| Query: | 493 | GSTLGL | 498 |
| Query: | 552 | GLPGTS | 557 |
| Query: | 570 | GSWDSR | 575 |
| Query: | 595 | GLKGND | 600 |
| Query: | 609 | GSSSSS | 614 |
| Query: | 898 | GQQVGC | 903 |

>PS00009|PDOC00009|AMIDATION Amidation site.

| | | | |
|---|---|---|---|
| Query: | 13 | PGRK | 16 |
| Query: | 467 | TGKR | 470 |
| Query: | 532 | PGKK | 535 |
| Query: | 841 | HGKR | 844 |
| Query: | 1038 | YGRK | 1041 |

>PS00290|PDOC00262|IG_MHC Immunoglobulins and major histocompatibility complex proteins signature.

| | | | |
|---|---|---|---|
| Query: | 376 | YSCHAGH | 382 |

>PS00973|PDOC00750|UCH_2_2 Ubiquitin carboxyl-terminal hydrolases family 2 signature 2.

| | | | |
|---|---|---|---|
| Query: | 365 | YGLYAVLVHSGYSCHAGHY | 383 |

FIG. 4D.

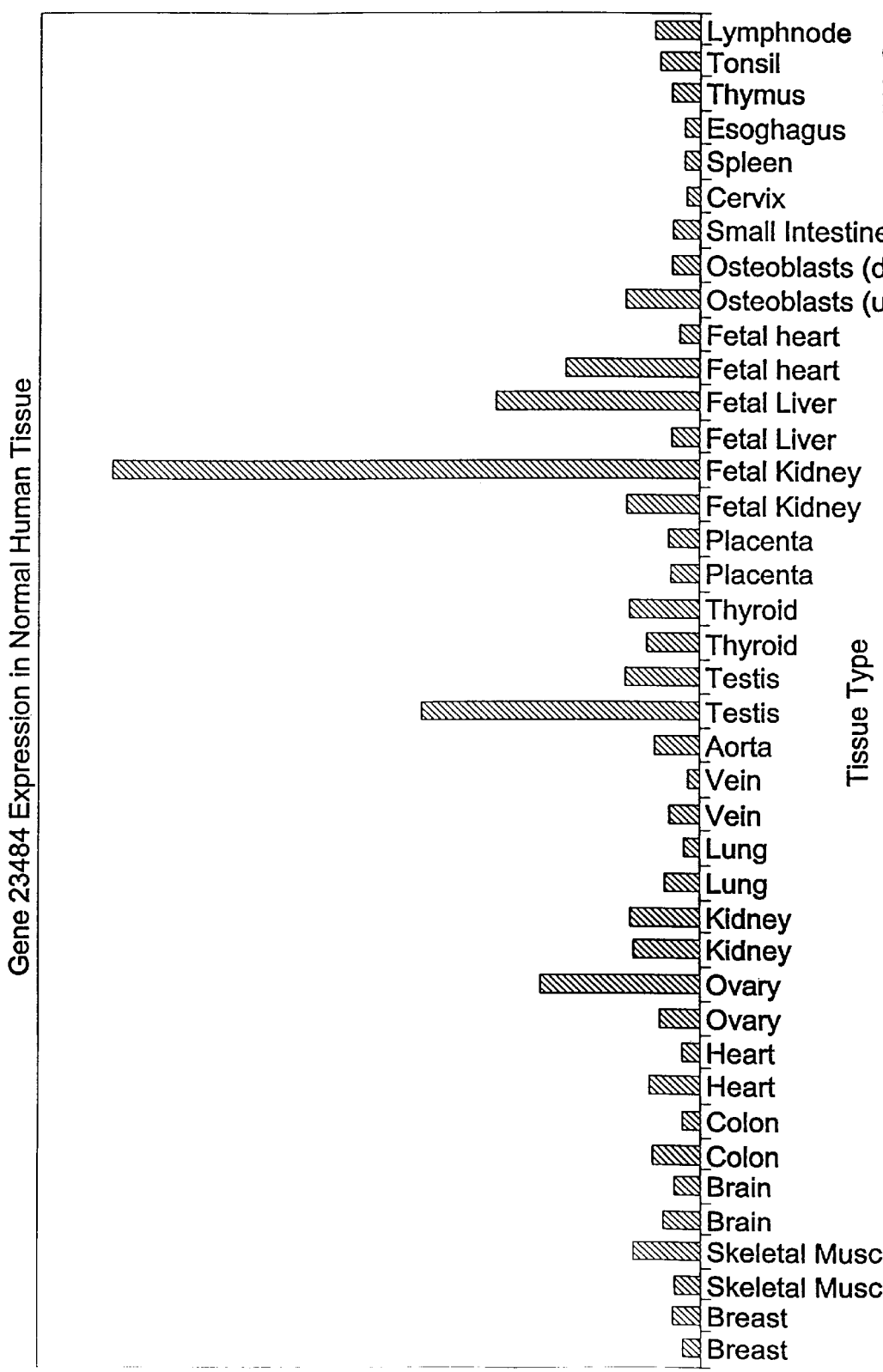

SEQUENCE LISTING

<160> NUMBER OF SEQ ID NOS: 2

<210> SEQ ID NO 1
<211> LENGTH: 1123
<212> TYPE: PRT
<213> ORGANISM: Homo sapiens

<400> SEQUENCE: 1

Met Pro Ile Val Asp Lys Leu Lys Glu Ala Leu Lys Pro Gly Arg Lys
1               5                   10                  15

Asp Ser Ala Asp Asp Gly Glu Leu Gly Lys Leu Leu Ala Ser Ser Ala
            20                  25                  30

Lys Lys Val Leu Leu Gln Lys Ile Glu Phe Glu Pro Ala Ser Lys Ser
        35                  40                  45

Phe Ser Tyr Gln Leu Glu Ala Leu Lys Ser Lys Tyr Val Leu Leu Asn
    50                  55                  60

Pro Lys Thr Glu Gly Ala Ser Arg His Lys Ser Gly Asp Asp Pro Pro
65                  70                  75                  80

Ala Arg Arg Gln Gly Ser Glu His Thr Tyr Glu Ser Cys Gly Asp Gly
                85                  90                  95

Val Pro Ala Pro Gln Lys Val Leu Phe Pro Thr Glu Arg Leu Ser Leu
            100                 105                 110

Arg Trp Glu Arg Val Phe Arg Val Gly Ala Gly Leu His Asn Leu Gly
        115                 120                 125

Asn Thr Cys Phe Leu Asn Ala Thr Ile Gln Cys Leu Thr Tyr Thr Pro
    130                 135                 140

Pro Leu Ala Asn Tyr Leu Leu Ser Lys Glu His Ala Arg Ser Cys His
145                 150                 155                 160

Gln Gly Ser Phe Cys Met Leu Cys Val Met Gln Asn His Ile Val Gln

```
                         165                 170                 175
Ala Phe Ala Asn Ser Gly Asn Ala Ile Lys Pro Val Ser Phe Ile Arg
                    180                 185                 190

Asp Leu Lys Lys Ile Ala Arg His Phe Arg Phe Gly Asn Gln Glu Asp
                195                 200                 205

Ala His Glu Phe Leu Arg Tyr Thr Ile Asp Ala Met Gln Lys Ala Cys
            210                 215                 220

Leu Asn Gly Cys Ala Lys Leu Asp Arg Gln Thr Gln Ala Thr Thr Leu
225                 230                 235                 240

Val His Gln Ile Phe Gly Gly Tyr Leu Arg Ser Arg Val Lys Cys Ser
                245                 250                 255

Val Cys Lys Ser Val Ser Asp Thr Tyr Asp Pro Tyr Leu Asp Val Ala
            260                 265                 270

Leu Glu Ile Arg Gln Ala Ala Asn Ile Val Arg Ala Leu Glu Leu Phe
                275                 280                 285

Val Lys Ala Asp Val Leu Ser Gly Glu Asn Ala Tyr Met Cys Ala Lys
            290                 295                 300

Cys Lys Lys Lys Val Pro Ala Ser Lys Arg Phe Thr Ile His Arg Thr
305                 310                 315                 320

Ser Asn Val Leu Thr Leu Ser Leu Lys Arg Phe Ala Asn Phe Ser Gly
                325                 330                 335

Gly Lys Ile Thr Lys Asp Val Gly Tyr Pro Glu Phe Leu Asn Ile Arg
                340                 345                 350

Pro Tyr Met Ser Gln Asn Asn Gly Asp Pro Val Met Tyr Gly Leu Tyr
                355                 360                 365

Ala Val Leu Val His Ser Gly Tyr Ser Cys His Ala Gly His Tyr Tyr
            370                 375                 380

Cys Tyr Val Lys Ala Ser Asn Gly Gln Trp Tyr Gln Met Asn Asp Ser
385                 390                 395                 400

Leu Val His Ser Ser Asn Val Lys Val Val Leu Asn Gln Gln Ala Tyr
                405                 410                 415

Val Leu Phe Tyr Leu Arg Ile Pro Gly Ser Lys Ser Pro Glu Gly
                420                 425                 430

Leu Ile Ser Arg Thr Gly Ser Ser Leu Pro Gly Arg Pro Ser Val
                435                 440                 445

Ile Pro Asp His Ser Lys Lys Asn Ile Gly Asn Gly Ile Ile Ser Ser
450                 455                 460

Pro Leu Thr Gly Lys Arg Gln Asp Ser Gly Thr Met Lys Lys Pro His
465                 470                 475                 480

Thr Thr Glu Glu Ile Gly Val Pro Ile Ser Arg Asn Gly Ser Thr Leu
                485                 490                 495

Gly Leu Lys Ser Gln Asn Gly Cys Ile Pro Pro Lys Leu Pro Ser Gly
                500                 505                 510

Ser Pro Ser Pro Lys Leu Ser Gln Thr Pro Thr His Met Pro Thr Ile
            515                 520                 525

Leu Asp Asp Pro Gly Lys Lys Val Lys Lys Pro Ala Pro Pro Gln His
            530                 535                 540

Phe Ser Pro Arg Thr Ala Gln Gly Leu Pro Gly Thr Ser Asn Ser Asn
545                 550                 555                 560

Ser Ser Arg Ser Gly Ser Gln Arg Gln Gly Ser Trp Asp Ser Arg Asp
                565                 570                 575

Val Val Leu Ser Thr Ser Pro Lys Leu Leu Ala Thr Ala Thr Ala Asn
            580                 585                 590
```

-continued

```
Gly His Gly Leu Lys Gly Asn Asp Glu Ser Ala Gly Leu Asp Arg Arg
            595                 600                 605

Gly Ser Ser Ser Ser Pro Glu His Ser Ala Ser Ser Asp Ser Thr
    610                 615                 620

Lys Ala Pro Gln Thr Pro Arg Ser Gly Ala Ala His Leu Cys Asp Ser
625                 630                 635                 640

Gln Glu Thr Asn Cys Ser Thr Ala Gly His Ser Lys Thr Pro Pro Ser
                645                 650                 655

Gly Ala Asp Ser Lys Thr Val Lys Leu Lys Ser Pro Val Leu Ser Asn
            660                 665                 670

Thr Thr Thr Glu Pro Ala Ser Thr Met Ser Pro Pro Ala Lys Lys
        675                 680                 685

Leu Ala Leu Ser Ala Lys Lys Ala Ser Thr Leu Trp Arg Ala Thr Gly
    690                 695                 700

Asn Asp Leu Arg Pro Pro Pro Ser Pro Ser Ser Asp Leu Thr His
705                 710                 715                 720

Pro Met Lys Thr Ser His Pro Val Val Ala Ser Thr Trp Pro Val His
                725                 730                 735

Arg Ala Arg Ala Val Ser Pro Ala Pro Gln Ser Ser Ser Arg Leu Gln
            740                 745                 750

Pro Pro Phe Ser Pro His Pro Thr Leu Leu Ser Ser Thr Pro Lys Pro
        755                 760                 765

Pro Gly Thr Ser Glu Pro Arg Ser Cys Ser Ser Ile Ser Thr Ala Leu
    770                 775                 780

Pro Gln Val Asn Glu Asp Leu Val Ser Leu Pro His Gln Leu Pro Glu
785                 790                 795                 800

Ala Ser Glu Pro Pro Gln Ser Pro Ser Glu Lys Arg Lys Lys Thr Phe
                805                 810                 815

Val Gly Glu Pro Gln Arg Leu Gly Ser Glu Thr Arg Leu Pro Gln His
            820                 825                 830

Ile Arg Glu Ala Thr Ala Ala Pro His Gly Lys Arg Lys Arg Lys Lys
        835                 840                 845

Lys Lys Arg Pro Glu Asp Thr Ala Ala Ser Ala Leu Gln Glu Gly Gln
    850                 855                 860

Thr Gln Arg Gln Pro Gly Ser Pro Met Tyr Arg Arg Glu Gly Gln Ala
865                 870                 875                 880

Gln Leu Pro Ala Val Arg Arg Gln Glu Asp Gly Thr Gln Pro Gln Val
                885                 890                 895

Asn Gly Gln Gln Val Gly Cys Val Thr Asp Gly His His Ala Ser Ser
            900                 905                 910

Arg Lys Arg Arg Arg Lys Gly Ala Glu Gly Leu Gly Glu Glu Gly Gly
        915                 920                 925

Leu His Gln Asp Pro Leu Arg His Ser Cys Ser Pro Met Gly Asp Gly
    930                 935                 940

Asp Pro Glu Ala Met Glu Glu Ser Pro Arg Lys Lys Lys Lys Lys
945                 950                 955                 960

Arg Lys Gln Glu Thr Gln Arg Ala Val Glu Glu Asp Gly His Leu Lys
                965                 970                 975

Cys Pro Arg Ser Ala Lys Pro Gln Asp Ala Val Val Pro Glu Ser Ser
            980                 985                 990

Ser Cys Ala Pro Ser Ala Asn Gly Trp Cys Pro Gly Asp Arg Met Gly
        995                 1000                1005
```

-continued

```
Leu Ser Gln Ala Pro Pro Val Ser Trp Asn Gly Glu Arg Glu Ser Asp
    1010                1015                1020
Val Val Gln Glu Leu Leu Lys Tyr Ser Ser Asp Lys Ala Tyr Gly Arg
1025                1030                1035                1040
Lys Val Leu Thr Trp Asp Gly Lys Met Ser Ala Val Ser Gln Asp Ala
                1045                1050                1055
Ile Glu Asp Ser Arg Gln Ala Arg Thr Glu Thr Val Val Asp Asp Trp
            1060                1065                1070
Asp Glu Glu Phe Asp Arg Gly Lys Glu Lys Lys Ile Lys Lys Phe Lys
        1075                1080                1085
Arg Glu Lys Arg Arg Asn Phe Asn Ala Phe Gln Lys Leu Gln Thr Arg
    1090                1095                1100
Arg Asn Phe Trp Ser Val Thr His Pro Ala Lys Ala Ala Ser Leu Ser
1105                1110                1115                1120
Tyr Arg Arg

<210> SEQ ID NO 2
<211> LENGTH: 3941
<212> TYPE: DNA
<213> ORGANISM: Homo sapiens
<220> FEATURE:
<221> NAME/KEY: CDS
<222> LOCATION: (279)...(3650)

<400> SEQUENCE: 2
cacgcgtccg ggcgccggag gcccggatgg tgcgcgtgct gggccgcggg ccgaaggagt      60
cgccagggct gcgtaggctt gtggcgcgcc cgcggagagg ccggggctct gacgcccgct     120
ctgcggcttc ggtgtttgaa caggccacag tccaggagcg cttacattca ggagctccgc     180
gtagcacctg cccaaccaaa ctcagccctc cgttaagatc ctggttccat gccgcagtag     240
gacagcaggc ccaagtctgc acatcccagt gatgcacc atg cca ata gtg gat aag     296
                                         Met Pro Ile Val Asp Lys
                                           1               5 ttg aag gag gcc ctg aaa ccc ggc cgc aag gac tcg gct gat gat gga     344
Leu Lys Glu Ala Leu Lys Pro Gly Arg Lys Asp Ser Ala Asp Asp Gly
             10                  15                  20 gaa ctg ggg aag ctt ctt gcc tcc tct gcc aag aag gtc ctt tta cag     392
Glu Leu Gly Lys Leu Leu Ala Ser Ser Ala Lys Lys Val Leu Leu Gln
         25                  30                  35 aaa atc gag ttc gag cca gcc agc aag agc ttc tcc tac cag ctg gag     440
Lys Ile Glu Phe Glu Pro Ala Ser Lys Ser Phe Ser Tyr Gln Leu Glu
     40                  45                  50 gcc tta aag agc aaa tat gtg ttg ctc aac ccc aaa aca gag gga gct     488
Ala Leu Lys Ser Lys Tyr Val Leu Leu Asn Pro Lys Thr Glu Gly Ala
 55                  60                  65                  70 agt cgc cac aag agt gga gat gac cca ccg gcc agg aga cag ggc agt     536
Ser Arg His Lys Ser Gly Asp Asp Pro Pro Ala Arg Arg Gln Gly Ser
                 75                  80                  85 gag cac acg tat gag agc tgt ggt gac gga gtc cca gcc ccg cag aaa     584
Glu His Thr Tyr Glu Ser Cys Gly Asp Gly Val Pro Ala Pro Gln Lys
             90                  95                 100 gtg ctt ttc ccc acg gag cga ctg tct ctg agg tgg gag cgg gtc ttc     632
Val Leu Phe Pro Thr Glu Arg Leu Ser Leu Arg Trp Glu Arg Val Phe
        105                 110                 115 cgc gtg ggc gca gga ctc cac aac ctt ggc aac acc tgc ttt ctc aat     680
Arg Val Gly Ala Gly Leu His Asn Leu Gly Asn Thr Cys Phe Leu Asn
    120                 125                 130 gcc acc atc cag tgc ttg acc tac aca cca cct cta gcc aac tac ctg     728
```

```
Ala Thr Ile Gln Cys Leu Thr Tyr Thr Pro Pro Leu Ala Asn Tyr Leu
135                     140                 145                 150 ctc tcc aag gag cat gct cgc agc tgc cac cag gga agc ttc tgc atg        776
Leu Ser Lys Glu His Ala Arg Ser Cys His Gln Gly Ser Phe Cys Met
                155                 160                 165 ctg tgt gtc atg cag aac cac att gtc cag gcc ttc gcc aac agc ggc        824
Leu Cys Val Met Gln Asn His Ile Val Gln Ala Phe Ala Asn Ser Gly
            170                 175                 180 aac gcc atc aag ccc gtc tcc ttc atc cga gac ctg aaa aag atc gcc        872
Asn Ala Ile Lys Pro Val Ser Phe Ile Arg Asp Leu Lys Lys Ile Ala
                185                 190                 195 cga cac ttc cgc ttt ggg aac cag gag gac gcg cat gag ttc ctg cgg        920
Arg His Phe Arg Phe Gly Asn Gln Glu Asp Ala His Glu Phe Leu Arg
        200                 205                 210 tac acc atc gac gcc atg cag aaa gcc tgc ctg aat ggc tgt gcc aag        968
Tyr Thr Ile Asp Ala Met Gln Lys Ala Cys Leu Asn Gly Cys Ala Lys
215                 220                 225                 230 ttg gat cgt caa acg cag gct act acc ttg gtc cat caa att ttt gga       1016
Leu Asp Arg Gln Thr Gln Ala Thr Thr Leu Val His Gln Ile Phe Gly
                235                 240                 245 ggg tat ctc aga tca cgc gtg aag tgc tcc gtg tgc aag agc gtc tcg       1064
Gly Tyr Leu Arg Ser Arg Val Lys Cys Ser Val Cys Lys Ser Val Ser
            250                 255                 260 gac acc tac gac ccc tac ttg gac gtc gcg ctg gag atc cgg caa gct       1112
Asp Thr Tyr Asp Pro Tyr Leu Asp Val Ala Leu Glu Ile Arg Gln Ala
            265                 270                 275 gcg aat att gtg cgt gct ctg gaa ctt ttt gtg aaa gca gat gtc ctg       1160
Ala Asn Ile Val Arg Ala Leu Glu Leu Phe Val Lys Ala Asp Val Leu
        280                 285                 290 agt gga gag aat gcc tac atg tgt gct aaa tgc aag aag aag gtt cca       1208
Ser Gly Glu Asn Ala Tyr Met Cys Ala Lys Cys Lys Lys Lys Val Pro
295                 300                 305                 310 gcc agc aag cgc ttc acc atc cac aga aca tcc aac gtc tta acc ctt       1256
Ala Ser Lys Arg Phe Thr Ile His Arg Thr Ser Asn Val Leu Thr Leu
                315                 320                 325 tcc ctc aag cgc ttt gcc aac ttc agc ggg ggg aag atc acc aag gat       1304
Ser Leu Lys Arg Phe Ala Asn Phe Ser Gly Gly Lys Ile Thr Lys Asp
                330                 335                 340 gta ggc tat ccg gaa ttc ctc aac ata cgt ccg tat atg tcc cag aat       1352
Val Gly Tyr Pro Glu Phe Leu Asn Ile Arg Pro Tyr Met Ser Gln Asn
            345                 350                 355 aat ggt gat cct gtc atg tat gga ctc tat gct gtc ctg gtg cac tcg       1400
Asn Gly Asp Pro Val Met Tyr Gly Leu Tyr Ala Val Leu Val His Ser
360                 365                 370 ggc tac agc tgc cat gcc ggg cac tat tac tgc tac gtg aag gca agc       1448
Gly Tyr Ser Cys His Ala Gly His Tyr Tyr Cys Tyr Val Lys Ala Ser
375                 380                 385                 390 aat gga cag tgg tac cag atg aat gat tcc ttg gtc cat tcc agc aac       1496
Asn Gly Gln Trp Tyr Gln Met Asn Asp Ser Leu Val His Ser Ser Asn
                395                 400                 405 gtc aag gtg gtt ctg aac cag cag gcc tac gtg ctg ttc tat ctg cga       1544
Val Lys Val Val Leu Asn Gln Gln Ala Tyr Val Leu Phe Tyr Leu Arg
            410                 415                 420 att cca ggc tct aag aaa agt ccc gag ggc ctc atc tcc agg aca ggc       1592
Ile Pro Gly Ser Lys Lys Ser Pro Glu Gly Leu Ile Ser Arg Thr Gly
            425                 430                 435 tcc tcc tcc ctt ccc ggc cgc ccg agt gtg att cca gat cac tcc aag       1640
Ser Ser Ser Leu Pro Gly Arg Pro Ser Val Ile Pro Asp His Ser Lys
440                 445                 450
```

```
aag aac atc ggc aat ggg att att tcc tcc cca ctg act gga aag cga    1688
Lys Asn Ile Gly Asn Gly Ile Ile Ser Ser Pro Leu Thr Gly Lys Arg
455                 460                 465                 470 caa gac tct ggg acg atg aag aag ccg cac acc act gaa gag att ggt    1736
Gln Asp Ser Gly Thr Met Lys Lys Pro His Thr Thr Glu Glu Ile Gly
            475                 480                 485 gtg ccc ata tcc agg aat ggc tcc acc ctg ggc ctg aag tcc cag aac    1784
Val Pro Ile Ser Arg Asn Gly Ser Thr Leu Gly Leu Lys Ser Gln Asn
        490                 495                 500 ggc tgc att cct cca aag ctg ccc tcg ggg tcc cct tcc ccc aaa ctc    1832
Gly Cys Ile Pro Pro Lys Leu Pro Ser Gly Ser Pro Ser Pro Lys Leu
    505                 510                 515 tcc cag aca ccc aca cac atg cca acc atc cta gac gac cct gga aag    1880
Ser Gln Thr Pro Thr His Met Pro Thr Ile Leu Asp Asp Pro Gly Lys
520                 525                 530 aag gtg aag aag cca gct cct cca cag cac ttt tcc ccc aga act gct    1928
Lys Val Lys Lys Pro Ala Pro Pro Gln His Phe Ser Pro Arg Thr Ala
535                 540                 545                 550 cag ggg ctg cct ggg acc agc aac tcg aat agc agc aga tct ggg agc    1976
Gln Gly Leu Pro Gly Thr Ser Asn Ser Asn Ser Ser Arg Ser Gly Ser
            555                 560                 565 caa agg cag ggc tcc tgg gac agc agg gat gtt gtc ctc tct acc tca    2024
Gln Arg Gln Gly Ser Trp Asp Ser Arg Asp Val Val Leu Ser Thr Ser
        570                 575                 580 cct aag ctc ctg gct aca gcc act gcc aac ggg cat ggg ctg aag ggg    2072
Pro Lys Leu Leu Ala Thr Ala Thr Ala Asn Gly His Gly Leu Lys Gly
    585                 590                 595 aac gac gag agc gct ggc ctc gac agg agg ggc tcc agc agc tcc agc    2120
Asn Asp Glu Ser Ala Gly Leu Asp Arg Arg Gly Ser Ser Ser Ser Ser
600                 605                 610 cca gag cac tcg gcc agc agc gac tcc acc aag gcc ccc cag acc ccc    2168
Pro Glu His Ser Ala Ser Ser Asp Ser Thr Lys Ala Pro Gln Thr Pro
615                 620                 625                 630 agg agt gga gcg gcc cat ctc tgc gat tct cag gaa acg aac tgt tcc    2216
Arg Ser Gly Ala Ala His Leu Cys Asp Ser Gln Glu Thr Asn Cys Ser
            635                 640                 645 acc gct ggc cac tcc aaa acg ccg cca agt gga gca gat tct aag acg    2264
Thr Ala Gly His Ser Lys Thr Pro Pro Ser Gly Ala Asp Ser Lys Thr
        650                 655                 660 gtg aag ctg aag tcc cct gtc ctg agc aac acc acc act gag cct gca    2312
Val Lys Leu Lys Ser Pro Val Leu Ser Asn Thr Thr Thr Glu Pro Ala
    665                 670                 675 agc acc atg tct cct cca cca gcc aaa aaa ctg gcc ctt tct gcc aag    2360
Ser Thr Met Ser Pro Pro Pro Ala Lys Lys Leu Ala Leu Ser Ala Lys
680                 685                 690 aag gcc agc acc ctg tgg agg gcg acc ggc aat gac ctc cgt cca cct    2408
Lys Ala Ser Thr Leu Trp Arg Ala Thr Gly Asn Asp Leu Arg Pro Pro
695                 700                 705                 710 ccc ccc tca cca tcc tcc gac ctc acc cac ccc atg aaa acc tct cac    2456
Pro Pro Ser Pro Ser Ser Asp Leu Thr His Pro Met Lys Thr Ser His
            715                 720                 725 ccc gtc gtt gcc tcc act tgg ccc gtc cat aga gcc agg gct gtg tca    2504
Pro Val Val Ala Ser Thr Trp Pro Val His Arg Ala Arg Ala Val Ser
        730                 735                 740 cct gct ccc caa tca tcc agc cgc ctg caa ccc ccc ttc agc ccc cac    2552
Pro Ala Pro Gln Ser Ser Ser Arg Leu Gln Pro Pro Phe Ser Pro His
    745                 750                 755 ccc aca ttg ctg tcc agt acc ccc aag ccc cca ggg acg tca gaa cca    2600
Pro Thr Leu Leu Ser Ser Thr Pro Lys Pro Pro Gly Thr Ser Glu Pro
760                 765                 770
```

```
cgg agc tgc tcc tcc atc tcg acg gcg ctg cct cag gtc aac gag gac    2648
Arg Ser Cys Ser Ser Ile Ser Thr Ala Leu Pro Gln Val Asn Glu Asp
775                 780                 785                 790 ctt gtg tct ctt cca cac cag ttg cca gag gcc agt gag ccc ccc cag    2696
Leu Val Ser Leu Pro His Gln Leu Pro Glu Ala Ser Glu Pro Pro Gln
        795                 800                 805 agc ccc tct gag aag agg aaa aag acc ttt gtg gga gag ccg cag agg    2744
Ser Pro Ser Glu Lys Arg Lys Lys Thr Phe Val Gly Glu Pro Gln Arg
            810                 815                 820 ctg ggc tca gag acg cgc ctc cca cag cac atc agg gag gcc act gcg    2792
Leu Gly Ser Glu Thr Arg Leu Pro Gln His Ile Arg Glu Ala Thr Ala
                825                 830                 835 gct ccc cac ggg aag agg aag agg aag aag aag cgc ccg gag gac         2840
Ala Pro His Gly Lys Arg Lys Arg Lys Lys Lys Arg Pro Glu Asp
    840                 845                 850 aca gct gcc agc gcc ctg cag gag ggg cag aca cag aga cag cct ggg    2888
Thr Ala Ala Ser Ala Leu Gln Glu Gly Gln Thr Gln Arg Gln Pro Gly
855                 860                 865                 870 agc ccc atg tac agg agg gag ggc cag gca cag ctg ccc gct gtc aga    2936
Ser Pro Met Tyr Arg Arg Glu Gly Gln Ala Gln Leu Pro Ala Val Arg
        875                 880                 885 cgg cag gaa gat ggc aca cag cca cag gtg aat ggc cag cag gtg gga    2984
Arg Gln Glu Asp Gly Thr Gln Pro Gln Val Asn Gly Gln Gln Val Gly
            890                 895                 900 tgt gtt acg gac ggc cac cac gcg agc agc agg aag cgg agg agg aaa    3032
Cys Val Thr Asp Gly His His Ala Ser Ser Arg Lys Arg Arg Arg Lys
                905                 910                 915 gga gca gaa ggt ctt ggt gaa gaa ggc ggc ctg cac cag gac cca ctt    3080
Gly Ala Glu Gly Leu Gly Glu Glu Gly Gly Leu His Gln Asp Pro Leu
    920                 925                 930 cgg cac agc tgc tct ccc atg ggt gat ggt gat cca gag gcc atg gaa    3128
Arg His Ser Cys Ser Pro Met Gly Asp Gly Asp Pro Glu Ala Met Glu
935                 940                 945                 950 gag tct cca agg aaa aag aaa aag aaa aga aag cag gag aca cag        3176
Glu Ser Pro Arg Lys Lys Lys Lys Lys Arg Lys Gln Glu Thr Gln
        955                 960                 965 cgg gca gta gaa gag gat ggg cat ctc aaa tgc cca agg agt gcc aag    3224
Arg Ala Val Glu Glu Asp Gly His Leu Lys Cys Pro Arg Ser Ala Lys
            970                 975                 980 ccc caa gat gct gtt gtc ccc gag tcc agc agc tgc gca cca tcc gcg    3272
Pro Gln Asp Ala Val Val Pro Glu Ser Ser Ser Cys Ala Pro Ser Ala
                985                 990                 995 aat ggc tgg tgt cct ggg gac cgc atg ggg ctg agc cag gcc cct cct    3320
Asn Gly Trp Cys Pro Gly Asp Arg Met Gly Leu Ser Gln Ala Pro Pro
    1000                1005                1010 gtg tct tgg aat gga gag cgg gag tct gat gtg gtc cag gaa ctg ctc    3368
Val Ser Trp Asn Gly Glu Arg Glu Ser Asp Val Val Gln Glu Leu Leu
1015                1020                1025                1030 aaa tac tca tct gat aaa gct tac ggg aga aaa gtt ctg acc tgg gat    3416
Lys Tyr Ser Ser Asp Lys Ala Tyr Gly Arg Lys Val Leu Thr Trp Asp
        1035                1040                1045 ggc aag atg tcg gcg gtc agt cag gat gct att gaa gac agc aga cag    3464
Gly Lys Met Ser Ala Val Ser Gln Asp Ala Ile Glu Asp Ser Arg Gln
            1050                1055                1060 gcc cgg act gag acc gtg gtt gat gac tgg gac gaa gag ttt gac cga    3512
Ala Arg Thr Glu Thr Val Val Asp Asp Trp Asp Glu Glu Phe Asp Arg
                1065                1070                1075 ggg aag gaa aag aaa att aaa aaa ttt aag aga gag aag agg aga aac    3560
Gly Lys Glu Lys Lys Ile Lys Lys Phe Lys Arg Glu Lys Arg Arg Asn
```

-continued

```
          1080                1085                1090
ttc aac gcc ttc cag aaa ctt cag act cga cgg aac ttc tgg tct gtg          3608
Phe Asn Ala Phe Gln Lys Leu Gln Thr Arg Arg Asn Phe Trp Ser Val
1095                1100                1105                1110 act cac cca gca aag gct gcc agc ctc agc tat cgc cgc tga                  3650
Thr His Pro Ala Lys Ala Ala Ser Leu Ser Tyr Arg Arg
                1115                1120 ctgtgcccct gtggaaggag atgatcaagc ggtgctgatt cacgagagtg gaagcctcca       3710
gagcttgggg ctttctggct gctcttcatt gacctgtgtg ttcccagcac acgaacagcg       3770
cccctaacgg agatttgttc agcgactgaa tatacacctg taaacgagta gcatgtatac       3830
attgattttg attacaaatg gttctgtatt ataccacc gttctgactg cttttttcac         3890
ttatagcttg gaaattgtct tctgttggta atacagaaat ctgtttcagt c                3941
```

23484, A NOVEL HUMAN UBIQUITIN PROTEASE

FIELD OF THE INVENTION

The present invention relates to a newly identified human ubiquitin protease belonging to the family of mammalian deubiquitinating enzymes. The invention also relates to polynucleotides encoding the ubiquitin protease. The invention further relates to methods using the ubiquitin protease polypeptides and polynucleotides as a target for diagnosis and treatment in ubiquitin-mediated or -related disorders. The invention further relates to drug-screening methods using the ubiquitin protease polypeptides and polynucleotides to identify agonists and antagonists for diagnosis and treatment. The invention further encompasses agonists and antagonists based on the ubiquitin protease polypeptides and polynucleotides. The invention further relates to procedures for producing the ubiquitin protease polypeptides and polynucleotides.

BACKGROUND OF THE INVENTION
The Ubiquitin System

Several biological processes are controlled by the ubiquitination of cellular protein. Cellular processes that are affected by ubiquitin modification include the regulation of gene expression, regulation of the cell cycle and cell division, cellular housekeeping, cell-specific metabolic pathways, disposal of mutated or post-translationally damaged proteins, the cellular stress response, modification of cell surface receptors, DNA repair, import of proteins into mitochondria, uptake of precursors into neurons, biogenesis of mitochondria, ribosomes, and peroxisomes, apoptosis, and growth factor-mediated signal transduction.

For some protein substrates ubiquitination leads to protein degradation by the 26S proteasomal complex. A wide variety of protein substrates are degraded by the 26S proteasomal complex following ubiquitination of the substrate. Degradation of a protein by the ubiquitin system involves two steps. The first involves the covalent attachment of multiple ubiquitin molecules to the substrate protein. The second involves degradation of the ubiquitinated protein by the 26S proteasome. In some cases, degradation of the ubiquitinated protein can occur by means of the lysosomal pathway.

The 26S proteasome comprises a 20S core catalytic complex which is flanked by two 19S regulatory complexes. The 26S complex recognizes ubiquitinated proteins. Substrate recognition by the 26S proteasome, however, may be mediated by the interaction of specific subunits of the 19S complex with the ubiquitin chain. The ubiquitinated protein is degraded by specific and energy-dependent proteases into free amino acids and free and reutilizable ubiquitin.

The 19S regulatory complex consists of many subunits that can be classified into ATPases and non-ATPases. This complex is thought to act in recognition, unfolding, and translocation of the substrates into the 20S proteasome for proteolysis. The regulatory complex contains isopeptidases capable of deubiquitinating substrates (Spataro et al. (1998) *British Journal of Cancer* 77:448–455).

The ubiquitin proteasome pathway functions to degrade abnormal proteins, short-lived normal proteins, long-lived normal proteins, and proteins of the endoplasmic recticulum. Important regulatory proteins rapidly inactivated by proteolysis include c-JUN, c-FOS, and p53 (Lecker et al. (1999) *Journal of Nutrition* 129:227S–237S). Conditions that stimulate protein degradation by the ubiquitin proteasome pathway include eating disorders, renal tubular defects, diabetes, uremia, neuromuscular disease, immobilization, burn injuries, sepsis, cancer, cachexia, hyperadrenocortisolism and hyperthyroidism.

Cellular proteins degraded by the ubiquitin system include cell cycle regulators, including mitotic cyclins, G1 cyclins, CDK inhibitors, anaphase inhibitors, transcription factors, tumor suppressors, and oncoproteins such as NF-κB and IκBα, p53, JUN, β-catenin, E2F-1, and membrane proteins such as Ste2p, GH receptor, T-cell receptor, platelet-derived growth factor, lymphocyte homing receptor, MET tyrosine kinase receptor, hepatocyte growth factor-scatter factor, connexin 43, the high affinity IgE receptor, the prolactin receptor, and the EGF receptor (Hershko et al. (1998) *Annual Review of Biochemistry* 67:425–479).

Ubiquitination does not only result in proteolytic degradation. For some protein substrates, ubiquitination is a reversible post-translational modification that can regulate cellular targeting and enzymatic activity. This includes targeting to the vacuole, activation of enzyme activity, such as Ikβ kinase activation, and activation of cytokine receptor-mediated signal transduction (D'Andrea et al. (1998) *Critical Reviews In Biochemistry and Molecular Biology* 33:337–352). The T-cell receptor undergoes ubiquitination in response to receptor engagement. Platelet derived growth factor undergoes multiple ubiquitination following ligand binding. Soluble steel factor has been shown to stimulate rapid polyubiquitination of the c-KIT receptor.

It has been shown that protein degradation accounts for regulation of proteins such as cyclins, cyclin-dependent kinase inhibitors, p53, c-JUN and c-FOS (Spitaro et al. above). The ubiquitin system has also shown to be involved in antigen presentation. The 26S proteasome is responsible for processing MHC-restricted class I antigens (Spitaro et al. above).

The ubiquitin system has been implicated in various diseases. One group includes pathology that results from loss of function, a mutation in an enzyme or substrate that leads to stabilization of the protein and consequent build up of a protein to abnormally high levels. The second involves pathologies that result from a gain of function that produces increased protein degradation.

The ubiquitin system has been implicated in various malignancies. In cervical carcinoma, low levels of p53 have been found. This protein is targeted for degradation by HPV E6-associated protein. Removal of the suppressor by this oncoprotein may be a mechanism utilized by the virus to transform cells. Other results have shown that c-JUN, but not the transforming counterpart, v-JUN, is ubiquitinated and subsequently degraded. Other studies show that low levels of p27, a cell division kinase inhibitor whose degradation is necessary for proper cell cycle progression, is correlated with colorectal, and breast carcinomas. The low level of this enzyme is due to activation of the ubiquitin system.

Human genetic diseases involving aberrant proteolysis have been reviewed (Kato (1999) *Human Mutation* 13:87–98). Cystic fibrosis has been correlated with the ubiquitin system. The cystic fibrosis transmembrane regulator in cystic fibrosis patients is almost completely degraded by the ubiquitin system so that an abnormally low amount of the wild type protein is found on the cell surface. In Angelman's syndrome, one of the enzymes involved in ubiquitination (E3) is affected. In Liddle syndrome, the E3 enzyme is also affected.

The ubiquitin system can also affect the immune and inflammatory response. The persistence of EBNA-1 contributes to some virus related pathologies. A sequence on this protein was found to inhibit degradation by the ubiquitin system. This inhibited processing and subsequent presentation of viral epitopes by SMC protein.

The ubiquitin system has also been implicated in neurodegenerative diseases. Ubiquitin immunohistochemistry has shown enrichment of ubiquitin conjugates in senile plaques, lysosomes, endosomes, and a variety of inclusion bodies and degenerative fibers in many neurodegenerative diseases, such as Alzheimer's, Parkinson's and Lewy body diseases, amyotrophic lateral sclerosis, and Creutzfeld-Jakob disease. Further, in Huntington disease and spinocerebellar ataxias, the proteins encoded by the affected genes aggregate in ubiquitin- and proteasome-positive intranuclear inclusion bodies.

The ubiquitin system has been associated with muscle wasting (Mitch et al. (1999) *American Journal of Physiology* 276: C1132–C1138 and Lecker et al. above) and muscle-wasting diseases and in such pathological states as fasting, starvation, sepsis, and denervation, all of which result from accelerated ubiquitin-mediated proteolysis (see Ciechanover, *EMBO Journal* 17:7151–7160 (1998)).

The ubiquitin system is also involved in development. The involvement in human brain development is indicated by the fact that a mutation in an E3 enzyme is implicated as the cause of Angelman's syndrome, a disorder characterized by mental retardation, seizures, and abnormal gait (Hershko et al. above).

The ubiquitin system is also associated with apoptosis. Ubiquitin-proteasome-mediated proteolysis is reported to play an important role in apoptosis of nerve growth factor-deprived neurons (Sadoul et al. (1996) *EMBO Journal* 15:3845–3852). One of the first genes shown to be involved in programmed cell death is the polyubiquitin gene that is regulated during metamorphosis of Manduca sexta. Radiation-induced apoptosis in human lymphocytes has been shown to be accompanied by increased ubiquitin mRNA and ubiquitinylated nuclear proteins. Further, drugs that interfere with proteasome function, such as lactacystin, prevent radiation-induced cell death of thymocytes (Hershko et al. above).

Deubiquitinating Enzymes

Deubiquitinating enzymes are cysteine proteases that specifically cleave ubiquitin conjugates at the ubiquitin carboxy terminus. These enzymes are responsible for processing linear polyubiquitin chains to generate free ubiquitin from precursor fusion proteins. They also affect pools of free ubiquitin by recycling branched chain ubiquitin. These enzymes also remove ubiquitin from ubiquitin- and polyubiquitin-conjugated target protein, thereby regulating localization or activity of the target. Further, these enzymes can remove ubiquitin from a ubiquitinated tagged protein and thereby rescue the protein from degradation by the 26S proteasome. The end result of each of these activities, is to affect the level of free intracellular ubiquitin (D'Andrea et al., above) and the level of specific proteins.

Ubiquitin is synthesized in a variety of functionally-distinct forms. One of these is a linear head-to-tail polyubiquitin precursor. Release of the free molecules involves specific enzymatic cleavage between the fused residues. The last ubiquitin moiety in many of these precursors is encoded with an extra C-terminal residue that must be removed to expose the active C-terminal Gly. In general, the recycling enzymes are thiol proteases that recognize the C-terminal domain/residue of ubiquitin. These are divided into two classes. The first is designated ubiquitin C-terminal hydrolase (UCH) and the second is designated ubiquitin-specific protease (UBP; isopeptidases) (Ciechanover, above). These enzymes have been reviewed in detail in D'Andrea, above.

UBPs contain six conserved regions. One surrounds the conserved cysteine, one surrounds the aspartic acid, one surrounds the histidine, and three additional regions of unknown function have been identified. These six domains provide a molecular signature for the UBP family. Short sequences surrounding the cysteine residue and histidine residue are highly conserved among all UBPs. Sequence comparison of several UBP family members reveals that there are various subfamilies. One subfamily, designated DUB, contains enzymes that are transcriptionally induced in response to cytokines. The UBP family contains enzymes whose members have multiple ubiquitin binding sites. Identified members of this family include DUB1, isoT, UBP3, Doa4, Tre2, and FAF (D'Andrea et al. above).

The UCH family is distinct from the UBP family. These enzymes are cysteine proteases but do not contain the six homology domains characteristic of the UBP family. Further, there is only one binding site for ubiquitin. With respect to substrate specificity, the UCH family preferentially cleaves ubiquitin from small molecules, such as peptides and amino acids. Further, the two families share little sequence homology with each other, although the UCH signature can be found in some UBPs.

The deubiquitinating enzymes can promote either degradation or stabilization of a given substrate. One of the best characterized deubiquitinating enzymes is the yeast UBP14p enzyme which has a human homolog designated isopeptidase-T. Isopeptidase-T hydrolyzes free polyubiquitin chains and stimulates degradation of polyubiquitinated protein substrates by the 26S proteasome. In vitro data suggest that the cellular role of isopeptidase-T is to dissemble unanchored polyubiquitin chains. The isopeptidase-T then sequentially degrades these polyubiquitin chains into ubiquitin monomers.

The yeast Doa4 promotes ubiquitin-mediated proteolysis of cellular substrates. The primary function appears to be the hydrolysis of isopeptide-linked ubiquitin chains from peptides that are the by-products of proteasome degradation. The function appears to be the clipping of polymeric ubiquitin from peptide degradation products. In summary, with respect to a degradation function, isopeptidases can produce free ubiquitin monomers from straight chain polyubiquitin, branched chain polyubiquitin, ubiquitin or polyubiquitin attached to substrate proteins, and ubiquitin or polyubiquitin attached to substrate remnants, such as peptides or amino acids.

Deubiquitinating enzymes that promote stabilization of substrates include the FAF protein. Results show that the FAF protein deubiquitinates and rescues a ubiquitin-conjugated target, preventing its degradation by the proteasome. Another deubiquitinating enzyme, designated PA700 isospeptidase, also prevents proteasome degradation. This enzyme has been isolated from the 19S regulatory complex. This enzyme appears to remove one ubiquitin at a time starting from the distal end of a polyubiquitin chain.

The enzymes have been associated with growth control. The mammalian oncoprotein Tre-2 is a member of the UBP superfamily. The transforming isoform of the Tre-2 oncoprotein is a truncated UPB lacking the histidine domain and lacking deubiquitinating activity. The full length Tre-2 protein has deubiquitinating activity but no transforming activity. Accordingly, it has been suggested that this protein acts as a growth suppressor within the cell.

Another UBP that regulates cellular function is designated DUB. DUB-1 was originally shown to be induced by interleukin-3 stimulation. It has been postulated that the DUB protein family is generally responsive to cytokines. It has also been shown that another family member, DUB-2, is induced by interleukin-2. Zhu et al. (1997) *Journal of Biological Chemistry* 272:51–57.

The enzymes may deubiquitinate cell surface growth factor receptors thereby prolonging receptor half life and amplifying growth signals. They may also deubiquitinate proteins involved in signal transduction and deubiquitinate cell cycle regulators such as cyclins or cyclin-CDK inhibitors. See D'Andrea above.

UBPs have also been linked to the chromatin regulatory process, transcriptional silencing. UBP-3 has been reported to complex with SIR-4, a trans-acting factor that is required for establishment and maintenance of silencing. Accordingly, UBP-3 may act as an inhibitor of silencing by either stabilizing an inhibitor or by removing a positive regulator.

The murine UNP protooncogene has been shown to encode a nuclear ubiquitin protease whose overexpression leads to oncogenic transformation in NIH3T3 cells. A cDNA was cloned corresponding to the human homolog of this gene. It was shown to map to a region frequently rearranged in human tumor cells. Further, it was shown that levels of this gene are elevated in small cell tumors and adenocarcinomas of the lung, suggesting a causative role of the gene in the neoplastic process (Gray et al. (1995) *Oncogene* 10:2179–2183).

A novel ubiquitin-specific protease, designated UBP-43, was cloned from a leukemia fusion protein in AML1-ETO Knockin mice. This protease was shown to function in hematopoitic cell differentiation. The overexpression of this gene was shown to block cytokine-induced terminal differentiation of monocytic cells (Liu et al. (1999) *Molecular and Cellular Biology* 19:3029–3038).

In summary, deubiquitinating enzymes are potentially powerful targets for modulating ubiquitination. Modulation of ubiquitination can increase or decrease the proteolysis of specific proteins, particularly key proteins in cellular processes, can increase or decrease levels of general proteolysis, thus affecting the basic metabolic state, and may increase or decrease the pool of free ubiquitin monomers available for ubiquitination.

Accordingly, ubiquitin proteases are a major target for drug action and development. Thus, it is valuable to the field of pharmaceutical development to identify and characterize previously unknown ubiquitin proteases. The present invention advances the state of the art by providing a previously unidentified human deubiquitinating enzyme.

SUMMARY OF THE INVENTION

It is an object of the invention to identify novel ubiquitin proteases.

It is a further object of the invention to provide novel ubiquitin protease polypeptides that are useful as reagents or targets in assays applicable to treatment and diagnosis of ubiquitin-mediated or -related disorders, especially disorders mediated by or related to deubiquitinating enzymes.

It is a further object of the invention to provide polynucleotides corresponding to the novel ubiquitin protease polypeptides that are useful as targets and reagents in assays applicable to treatment and diagnosis of ubiquitin or ubiquitin protease-mediated or -related disorders and useful for producing novel ubiquitin protease polypeptides by recombinant methods.

A specific object of the invention is to identify compounds that act as agonists and antagonists and modulate the expression of the novel ubiquitin protease.

A further specific object of the invention is to provide compounds that modulate expression of the ubiquitin protease for treatment and diagnosis of ubiquitin and ubiquitin protease-related disorders.

The invention is thus based on the identification of a novel human ubiquitin protease. The amino acid sequence is shown in SEQ ID NO 1. The nucleotide sequence is shown in SEQ ID NO 2.

The invention provides isolated ubiquitin protease polypeptides, including a polypeptide having the amino acid sequence shown in SEQ ID NO 1 or the amino acid sequence encoded by the cDNA deposited as ATCC No. PTA-1849 on May 9, 2000 ("the deposited cDNA"), or as ATCC No. PTA-1849 on May 9, 2000 ("the deposited cDNA").

The invention also provides isolated ubiquitin protease nucleic acid molecules having the sequence shown in SEQ ID NO 2 or in the deposited cDNA.

The invention also provides variant polypeptides having an amino acid sequence that is substantially homologous to the amino acid sequence shown in SEQ ID NO 1 or encoded by the deposited cDNA.

The invention also provides variant nucleic acid sequences that are substantially homologous to the nucleotide sequence shown in SEQ ID NO 2 or in the deposited cDNA.

The invention also provides fragments of the polypeptide shown in SEQ ID NO 1 and nucleotide sequence shown in SEQ ID NO 2, as well as substantially homologous fragments of the polypeptide or nucleic acid.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the ubiquitin protease nucleic acid molecules and polypeptides, and particularly recombinant vectors and host cells.

The invention also provides methods of making the vectors and host cells and methods for using them to produce the ubiquitin protease nucleic acid molecules and polypeptides.

The invention also provides antibodies or antigen-binding fragments thereof that selectively bind the ubiquitin protease polypeptides and fragments.

The invention also provides methods of screening for compounds that modulate expression or activity of the ubiquitin protease polypeptides or nucleic acid (RNA or DNA).

The invention also provides a process for modulating ubiquitin protease polypeptide or nucleic acid expression or activity, especially using the screened compounds. Modulation may be used to treat conditions related to aberrant activity or expression of the ubiquitin protease polypeptides or nucleic acids or of the ubiquitin system. In addition, modulation may be used to treat conditions, such as viral infection, that are affected by the ubiquitin protease.

The invention also provides assays for determining the activity of or the presence or absence of the ubiquitin protease polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DESCRIPTION OF THE DRAWINGS

FIG. 1 shows the nucleotide sequence (SEQ ID NO 2) and the deduced amino acid sequence (SEQ ID NO 1) of the novel ubiquitin protease. The underlined amino acids designate the conserved cysteine region and conserved histidine region. These regions are conserved among thiol protease members of the UBP and UCH protein families.

FIG. 4 shows an analysis of the ubiquitin protease open reading frame for amino acids corresponding to specific functional sites (SEQ ID NO:1). Glycosylation sites are found from about amino acid 134 to 137, with the modified amino acid at position 134; about amino acid 333 to 336, with the modified amino acid at position 333; from about amino acid 398 to 401 with the modified amino acid at position 398, from about 492 to 495 with the modified amino acid at position 492, from about 560 to 563 with the modified amino acid at position 560, from about 644 to 647 with the modified amino acid at position 644, and from about 672 to 675 with the modified amino acid at position 672. Cyclic AMP and cyclic GMP-dependent protein kinase phosphorylation sites are found from about amino acid 15 to 18 with the modified amino acid at position 18, from about amino acid 313 to 316 with the modified amino acid at position 316, from about 607 to 610 with the modified amino acid at position 610; from about amino acid 694 to 697 with the modified amino acid at position 697; from about amino acid 812 to 815 with the modified amino acid at position 815. Protein kinase C phosphorylation sites are found from about amino acid 31 to 33, with the modified amino acid at position 31; from about amino acid 107 to 109, with the modified amino acid at position 107; from about amino acid 111 to 113, with the modified amino acid at position 111; from about amino acid 312 to 314, with the modified amino acid at position 312; from about amino acid 327 to 329, with the modified amino acid at position 327; from about amino acid 426 to 428, with the modified amino acid at position 426; from about amino acid 453 to 455, with the modified amino acid at position 453; from about amino acid 467 to 469, with the modified amino acid at position 467; from about amino acid 475 to 477, with the modified amino acid at position 475; from about amino acid 515 to 517, with the modified amino acid at position 515; from about amino acid 546 to 548, with the modified amino acid at position 546; from about amino acid 561 to 563, with the modified amino acid at position 561; from about amino acid 556 to 568, with the modified amino acid at position 566; from about amino acid 582 to 584, with the modified amino acid at position 582; from about amino acid 623 to 625, with the modified amino acid at position 623; from about amino acid 629 to 631, with the modified amino acid at position 629; from about amino acid 662 to 664, with the modified amino acid at position 662; from about 692 to 694, with the modified amino acid at position 692; from about amino acid 748 to 750, with the modified amino acid at position 748; from about amino acid 765 to 767, with the modified amino acid at position 765; from about amino acid 809 to 811, with the modified amino acid at position 809; from about amino acid 865 to 867, with the modified amino acid at position 865; from about amino acid 911 to 913, with the modified amino acid at position 911; from about amino acid 952 to 954, with the modified amino acid at position 952; from about amino acid 965 to 967, with the modified amino acid at position 965; from about amino acid 980 to 982, with the modified amino acid at position 980; from about amino acid 1034 to 1036, with the modified amino acid at position 1034; from about amino acid 1103 to 1105, with the modified amino acid at position 1103; and from about amino acid 1120 to 1122, with the modified amino acid at 1120. Casein kinase II phophorylation sites are found from about amino acid 18 to 21; from amino acid 75 to 78; from amino acid 92 to 95; from amino acid 260 to 263; from amino acid 481 to 484; from amino acid 527 to 530; from amino acid 613 to 616; from amino acid 656 to 659; from amino acid 673 to 676; from amino acid 703 to 706; from amino acid 807 to 810; and from amino acid 1067 to 1070. Tyrosine kinase phosphorylation sites are found from about amino acid 83 to 90, with the modified amino acid at position 90; from about amino acid 338 to 345, with the modified amino acid at position 345; and from about amino acid 1031 to 1038, with the modified amino acid at position 1038. N-myristoylation sites are found from about amino acid from about 85 to 90, with the modified amino acid at position 85; from about amino acid 336 to 341, with the modified amino acid at position 336; from about amino acid 486 to 491, with the modified amino acid at position 486, from about amino acid 493 to 498, with the modified amino acid at position 493, from about amino acid 552 to 557, with the modified amino acid at position 552; from amino acid 570 to 575, with the modified amino acid at position 570; from amino acid 595 to 600, with the modified amino acid at position 595; from amino acid 609 to 614, with the modified amino acid at position 609; and from amino acid 898 to 903, with the modified amino acid at position 898. Amidation sites are found from about amino acid 13 to 16, from about amino acid 467 to 470, from about amino acid 532 to 535; from about amino acid 841 to 844; and from about amino acids 1038 to 1041. In addition, an amino acid signature corresponding to the MHC immunoglobulins and major histocompatibility complex proteins is found from amino acids 376 to 382. The amino acids corresponding to the UCH family 2 signature are found at amino acids 365–383.

FIG. 6 shows expression of the protease in various tissues and cell types in culture. The expression data was derived from RT-PCR of various cDNA libraries.

DETAILED DESCRIPTION OF THE INVENTION

Polypeptides

The invention is based on the identification of a novel human ubiquitin protease. Specifically, an expressed sequence tag (EST) was selected based on homology to ubiquitin protease sequences. This EST was used to design primers based on sequences that it contains and used to identify a cDNA from a human prostate library. Positive clones were sequenced and the overlapping fragments were assembled. Analysis of the assembled sequence revealed that the cloned cDNA molecule encodes a ubiquitin protease containing the conserved amino acid residues found in UBP and UCH thiol proteases.

The invention thus relates to a novel ubiquitin protease having the deduced amino acid sequence shown in FIG. 1

(SEQ ID NO 1) or having the amino acid sequence encoded by the deposited cDNA, ATCC No. PTA-1849 on May 9, 2000.

The deposits will be maintained under the terms of the Budapest Treaty on the International Recognition of the Deposit of Microorganisms. The deposits are provided as a convenience to those of skill in the art and is not an admission that a deposit is required under 35 U.S.C. §112. The deposited sequences, as well as the polypeptides encoded by the sequences, are incorporated herein by reference and controls in the event of any conflict, such as a sequencing error, with description in this application. "Ubiquitin protease polypeptide" or "ubiquitin protease protein" refers to the polypeptide in SEQ ID NO 1 or encoded by the deposited cDNA. The term "ubiquitin protease protein" or "ubiquitin protease polypeptide", however, further includes the numerous variants described herein, as well as fragments derived from the full-length ubiquitin proteases and variants.

Figure 5:
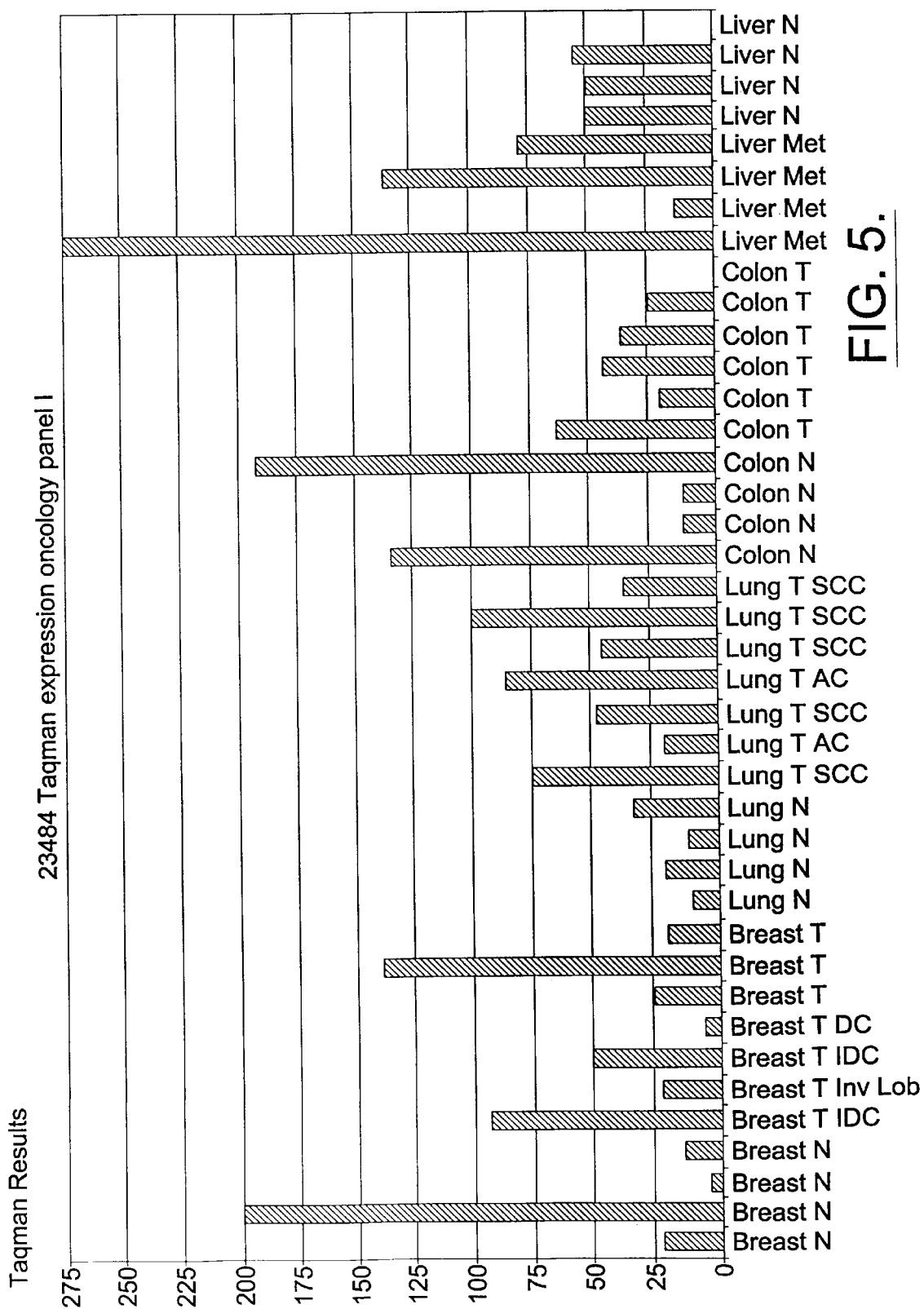
FIG. 5 shows expression of the protease in normal and malignant breast, lung, liver and colon tissues. The liver metastases are derived from malignant colonic tissue.

Tissues and/or cells in which the ubiquitin protease is expressed include, but are not limited to those shown in FIGS. 5 and 6. Tissues in which the gene is highly expressed include fetal kidney, testes, fetal liver, ovary, and fetal heart. Expression is also seen in the kidney, thyroid, undifferentiated osteoblasts and skeletal muscle. The ubiquitin protease is also expressed in normal liver and in normal and malignant breast, lung, and colon tissue and in liver metastases derived from malignant colonic tissues. Hence, the ubiquitin protease is relevant to disorders involving the tissues in which it is expressed, especially in breast, lung, colon, and colon metastases to liver. Expression has been confirmed by Northern blot analysis.

The present invention thus provides an isolated or purified ubiquitin protease polypeptide and variants and fragments thereof Based on a BLAST search, highest homology was shown to Ubiquitin Carboxyl-terminal hydrolase (AL03 1525) from *S. pombe*.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The ubiquitin protease polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the ubiquitin protease having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

A ubiquitin protease polypeptide is also considered to be isolated when it is part of a membrane preparation or is purified and then reconstituted with membrane vesicles or liposomes.

The language "substantially free of chemical precursors or other chemicals" includes preparations of the ubiquitin protease polypeptide in which it is separated from chemical precursors or other chemicals that are involved in its synthesis. In one embodiment, the language "substantially free of chemical precursors or other chemicals," includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the ubiquitin protease polypeptide comprises the amino acid sequence shown in SEQ ID NO 1. However, the invention also encompasses sequence variants. Variants include a substantially homologous protein encoded by the same genetic locus in an organism, i.e., an allelic variant.

Variants also encompass proteins derived from other genetic loci in an organism, but having substantial homology to the ubiquitin protease of SEQ ID NO 1. Variants also include proteins substantially homologous to the ubiquitin protease but derived from another organism, i.e., an ortholog. Variants also include proteins that are substantially homologous to the ubiquitin protease that are produced by chemical synthesis. Variants also include proteins that are substantially homologous to the ubiquitin protease that are produced by recombinant methods. It is understood, however, that variants exclude any amino acid sequences disclosed prior to the invention.

As used herein, two proteins (or a region of the proteins) are substantially homologous when the amino acid sequences are at least about 70–75%, typically at least about 80–85%, and most typically at least about 90–95% or more homologous. A substantially homologous amino acid sequence, according to the present invention, will be encoded by a nucleic acid sequence hybridizing to the nucleic acid sequence, or portion thereof, of the sequence shown in SEQ ID NO 2 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (i.e., 100%=the entire coding sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the ubiquitin protease. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247:1306–1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci. USA* 90:5873–5877. Such an algorithm is incorporated into the NBLAST and XBLAST programs (version 2.0) as described in Altschul et al. (1997) *Nucleic Acids Res.* 25:3389–3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444–453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res.* 12(1):387) using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3–5; and FASTA described in Pearson et al. (1988) *PNAS* 85:2444–8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of ubiquitin binding, ubiquitin recognition, interaction with ubiquitinated substrate protein, such as binding or proteolysis, subunit interaction, particularly within the proteasome, activation or binding by ATP, developmental expression, temporal expression, tissue-specific expression, interacting with cellular components, such as transcriptional regulatory factors, and particularly trans-acting transcriptional regulatory factors, proteolytic cleavage of peptide bonds in polyubiquitin and peptide bonds between ubiquitin or polyubiquitin and substrate protein, and proteolytic cleavage of peptide bonds between ubiquitin or polyubiquitin and a peptide or amino acid.

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the ubiquitin protease polypeptide. This includes preventing immunogenicity from pharmaceutical formulations by preventing protein aggregation.

Useful variations further include alteration of catalytic activity. For example, one embodiment involves a variation at the binding site that results in binding but not hydrolysis, or slower hydrolysis, of the peptide bond. A further useful variation results in an increased rate of hydrolysis of the peptide bond. A further useful variation at the same site can result in higher or lower affinity for substrate. Useful variations also include changes that provide for affinity for a different ubiquitinated substrate protein than that normally recognized. Other useful variations involving altered recognition affect recognition of the type of substrate normally recognized. For example, one variation could result in recognition of ubiquitinated intact substrate but not of substrate remnants, such as ubiquitinated amino acid or peptide that are proteolysis products that result from the hydrolysis of the intact ubiquitinated substrate. Alternatively, the protease could be varied so that one or more of the remnant products is recognized but not the intact protein substrate. Another variation would affect the ability of the protease to rescue a ubiquitinated protein. Thus, protein substrates that are normally rescued from proteolysis would be subject to degradation. Further useful variations affect the ability of the protease to be induced by activators, such as cytokines, including but not limited to, those disclosed herein. Another useful variation would affect the recognition of ubiquitin substrate so that the enzyme could not recognize one or more of a linear polyubiquitin, branched chain polyubiquitin, linear polyubiquitinated substrate, or branched chain polyubiquitin substrate. Specific variations include truncation in which, for example, a HIS domain is deleted, the variation resulting in decrease or loss of deubiquitination activity. Another useful variation includes one that prevents activation by ATP. Another useful variation provides a fusion protein in which one or more domains or subregions are operationally fused to one or more domains or subregions from another UBP or from a UCH. Specifically, a domain or subregion can be introduced that provides a rescue function to an enzyme not normally having this function or for recognition of a specific substrate wherein recognition is not available to the original enzyme. Other variations include those that affect ubiquitin recognition or recognition of a ubiquitinated substrate protein. Further variations could affect specific subunit interaction, particularly in the proteasome. Other variations would affect developmental, temporal, or tissue-specific expression. Other variations would affect the interaction with cellular components, such as transcriptional regulatory factors.

Amino acids that are essential for function can be identified by methods known in the art, such as site-directed mutagenesis or alanine-scanning mutagenesis (Cunningham et al. (1985) *Science* 244:1081–1085). The latter procedure introduces single alanine mutations at every residue in the molecule. The resulting mutant molecules are then tested for biological activity, such as peptide hydrolysis in vitro or ubiquitin-dependent in vitro activity, such as proliferative activity, receptor-mediated signal transduction, and other cellular processes including, but not limited, those disclosed herein that are a function of the ubiquitin system. Sites that are critical for binding or recognition can also be determined by structural analysis such as crystallization, nuclear magnetic resonance or photoaffinity labeling (Smith et al. (1992) *J. Mol. Biol.* 224:899–904; de Vos et al (1992) *Science* 255:306–312).

The assays for deubiquitinating enzyme activity are well known in the art and can be found, for example, in Zhu et al. (1997) *Journal of Biological Chemistry* 272:51–57, Mitch et al. (1999) *American Journal of Physiology* 276: C1132–C1138, Liu et al. (1999) *Molecular and Cell Biology* 19:3029–3038, and such as those cited in various reviews, for example, Ciechanover et al. (1994) *The FASEB Journal* 8:182–192, Chiechanover (1994) *Biol. Chem. Hoppe-Seyler* 375:565–581, Hershko et al. (1998) *Annual Review of Biochemistry* 67:425–479, Swartz (1999) *Annual Review of Medicine* 50:57–74, Ciechanover (1998) *EMBO Journal* 17:7151–7160, and D'Andrea et al. (1998) *Critical Reviews in Biochemistry and Molecular Biology* 33:337–352. These assays include, but are not limited to, the disappearance of substrate, including decrease in the amount of polyubiquitin or ubiquitinated substrate protein or protein remnant, appearance of intermediate and end products, such as appearance of free ubiquitin monomers, general protein turnover, specific protein turnover, ubiquitin binding, binding to ubiquitinated substrate protein, subunit interaction, interaction with ATP, interaction with cellular components such as trans-acting regulatory factors, stabilization of specific proteins, and the like.

Substantial homology can be to the entire nucleic acid or amino acid sequence or to fragments of these sequences.

The invention thus also includes polypeptide fragments of the ubiquitin protease. Fragments can be derived from the amino acid sequence shown in SEQ ID NO 1. However, the invention also encompasses fragments of the variants of the ubiquitin proteases as described herein.

The fragments to which the invention pertains, however, are not to be construed as encompassing fragments that may be disclosed prior to the present invention.

Accordingly, a fragment can comprise at least about 11, 15, 20, 25, 30, 35, 40, 45, 50 or more contiguous amino acids. Fragments can retain one or more of the biological activities of the protein, for example the ability to bind to ubiquitin or hydrolyze peptide bonds, as well as fragments that can be used as an immunogen to generate ubiquitin protease antibodies.

Biologically active fragments (peptides which are, for example, 5, 7, 10, 12, 15, 20, 30, 35, 36, 37, 38, 39, 40, 50, 100 or more amino acids in length) can comprise a domain or motif e.g., catalytic site, UCH family 2 signature, signature for the immunoglobulin and major histocompatibility complex proteins, and sites for glycosylation, cAMP and cGMP-dependent protein kinase phosphorylation, protein kinase C phosphorylation, casein kinase II phosphorylation, tyrosine kinase phosphorylation, N-myristoylation, and amidation. Further possible fragments include the catalytic site or domain including conserved amino acid residues found in UBP and UCH thiol proteases. Such regions include, for example, about amino acids 123 to 1313 of SEQ ID NO 1 or the UCH2 family 2 signature found from about amino acids 365 to about 383 of SEQ ID NO 1. Additional domains include ubiquitin recognition sites, ubiquitin binding sites, sites important for subunit interaction, and sites important for carrying out the other functions of the protease as described herein.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the ubiquitin protease and variants. These epitope-bearing peptides are useful to raise antibodies that bind specifically to a ubiquitin protease polypeptide or region or fragment. These peptides can contain at least 11, 12, at least 14, or between at least about 15 to about 30 amino acids.

Figure 2:
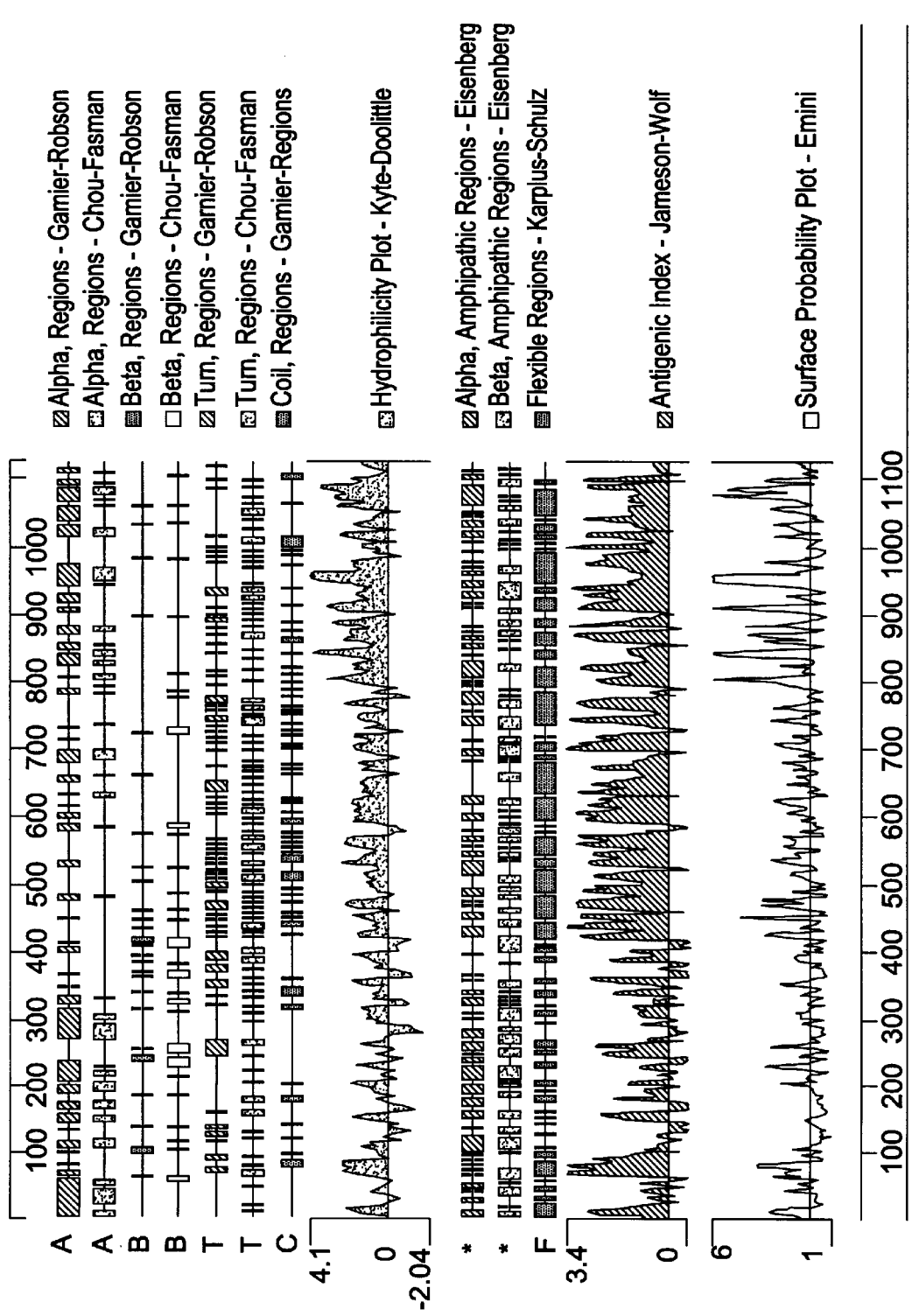
FIG. 2 shows an analysis of the ubiquitin protease amino acid sequence: αβturn and coil regions; hydrophilicity; amphipathic regions; flexible regions; antigenic index; and surface probability plot.
Figure 3:
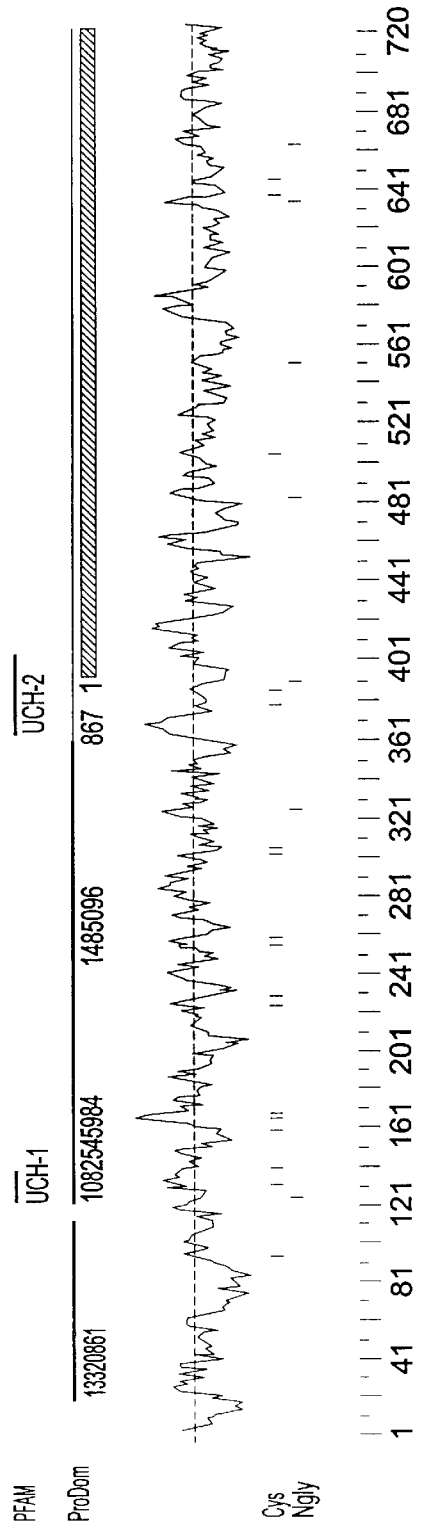
FIG. 3 shows a hydrophobicity plot of the ubiquitin protease (SEQ ID NO:1).

Non-limiting examples of antigenic polypeptides that can be used to generate antibodies include but are not limited to peptides derived from an extracellular site. Regions having a high antigenicity index are shown in FIG. 2. However, intracellularly-made antibodies ("intrabodies") are also encompassed, which would recognize intracellular peptide regions.

The epitope-bearing ubiquitin protease polypeptides may be produced by any conventional means (Houghten, R. A. (1985) *Proc. Natl. Acad. Sci. USA* 82:5131–5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the ubiquitin protease fragment and an additional region fused to the carboxyl terminus of the fragment.

The invention thus provides chimeric or fusion proteins. These comprise a ubiquitin protease peptide sequence operatively linked to a heterologous peptide having an amino acid sequence not substantially homologous to the ubiquitin protease. "Operatively linked" indicates that the ubiquitin protease peptide and the heterologous peptide are fused in-frame. The heterologous peptide can be fused to the N-terminus or C-terminus of the ubiquitin protease or can be internally located.

In one embodiment the fusion protein does not affect ubiquitin protease function per se. For example, the fusion protein can be a GST-fusion protein in which the ubiquitin protease sequences are fused to the C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant ubiquitin protease. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52–58 (1995) and Johanson et al. *J. Biol. Chem.* 270:9459–9471). Thus, this invention also encompasses soluble fusion proteins containing a ubiquitin protease polypeptide and various portions of the constant regions of heavy or light chains of immunoglobulins of various subclass (IgG, IgM, IgA, IgE). Preferred as immunoglobulin is the constant part of the heavy chain of human IgG, particularly IgG 1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). A ubiquitin protease-encoding nucleic acid can be cloned into such an expression vector such that the fusion moiety is linked in-frame to the ubiquitin protease.

Another form of fusion protein is one that directly affects ubiquitin protease functions. Accordingly, a ubiquitin protease polypeptide is encompassed by the present invention in which one or more of the ubiquitin protease domains (or parts thereof) has been replaced by homologous domains (or parts thereof) from another UBP or UCH species. Accordingly, various permutations are possible. One or more functional sites as disclosed herein from the specifically disclosed protease can be replaced by one or more functional sites from a corresponding UBP family member or from a UCH family member. Thus, chimeric ubiquitin proteases can be formed in which one or more of the native domains or subregions has been replaced by another.

Additionally, chimeric ubiquitin protease proteins can be produced in which one or more functional sites is derived from a different ubiquitin protease family. It is understood however that sites could be derived from ubiquitin protease families that occur in the mammalian genome but which have not yet been discovered or characterized. Such sites include but are not limited to any of the functional sites disclosed herein.

The isolated ubiquitin proteases can be purified from any of the cells that naturally express it, such as, fetal kidney, testes, fetal liver, ovary, fetal heart, kidney, thyroid, undifferentiated osteoblasts, skeletal muscle, malignant breast tissue, primary lung tumors and liver metastases derived from colon. Alternatively, the ubiquitin protease may be purified from cells that have been altered to express it (recombinant), or synthesized using known protein synthesis methods.

In one embodiment, the protein is produced by recombinant DNA techniques. For example, a nucleic acid molecule encoding the ubiquitin protease polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (1990) *Meth. Enzymol.* 182: 626–646) and Rattan et al. (1992) *Ann. N.Y. Acad. Sci.* 663:48–62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in E coli, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous, to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

The ubiquitin protease polypeptides are useful for producing antibodies specific for the ubiquitin protease, regions, or fragments. Regions having a high antigenicity index score are shown in FIG. 2.

The ubiquitin protease polypeptides are useful for biological assays related to ubiquitin protease function. Such assays involve any of the known functions or activities or properties useful for diagnosis and treatment of ubiquitin- or ubiquitin protease-related conditions or conditions in which expression of the protease is relevant, such as in viral infections. Potential assays have been disclosed herein and generically include disappearance of substrate, appearance of end product, and general or specific protein turnover.

The ubiquitin protease polypeptides are also useful in drug screening assays, in cell-based or cell-free systems. Cell-based systems can be native, i.e., cells that normally express the ubiquitin protease, as a biopsy or expanded in cell culture. In one embodiment, however, cell-based assays involve recombinant host cells expressing the ubiquitin protease.

Determining the ability of the test compound to interact with the ubiquitin protease can also comprise determining the ability of the test compound to preferentially bind to the polypeptide as compared to the ability of a known binding molecule (e.g., ubiquitin) to bind to the polypeptide.

The polypeptides can be used to identify compounds that modulate ubiquitin protease activity. Such compounds, for example, can increase or decrease affinity for polyubiquitin, either linear or branched chain, ubiquitinated protein substrate, or ubiquitinated protein substrate remnants. Such compounds could also, for example, increase or decrease the rate of binding to these components. Such compounds could also compete with these components for binding to the ubiquitin protease or displace these components bound to the ubiquitin protease. Such compounds could also affect interaction with other components, such as ATP, other subunits, for example, in the 19S complex, and transcriptional regulatory factors. It is understood, therefore, that such compounds can be identified not only by means of ubiquitin, but by means of any of the components that functionally interact with the disclosed protease. This includes, but is not limited to, any of those components disclosed herein.

Both ubiquitin protease and appropriate variants and fragments can be used in high-throughput screens to assay candidate compounds for the ability to bind to the ubiquitin protease. These compounds can be further screened against a functional ubiquitin protease to determine the effect of the compound on the ubiquitin protease activity. Compounds can be identified that activate (agonist) or inactivate (antagonist) the ubiquitin protease to a desired degree. Modulatory methods can be performed in vitro (e.g., by culturing the cell with the agent) or, alternatively, in vivo (e.g., by administering the agent to a subject).

The ubiquitin protease polypeptides can be used to screen a compound for the ability to stimulate or inhibit interaction between the ubiquitin protease protein and a target molecule that normally interacts with the ubiquitin protease protein. The target can be ubiquitin, ubiquitinated substrate, or polyubiquitin or another component of the pathway with which the ubiquitin protease protein normally interacts (for example, ATP). The assay includes the steps of combining the ubiquitin protease protein with a candidate compound under conditions that allow the ubiquitin protease protein or fragment to interact with the target molecule, and to detect the formation of a complex between the ubiquitin protease protein and the target or to detect the biochemical consequence of the interaction with the ubiquitin protease and the target. Any of the associated effects of protease function can be assayed. This includes the production of hydrolysis products, such as free terminal peptide substrate, free terminal amino acid from the hydrolyzed substrate, free ubiquitin, lower molecular weight species of hydrolyzed polyubiquitin, released intact substrate protein resulting from rescue from proteolysis, free polyubiquitin formed from hydrolysis of the polyubiquitin from intact substrate, and substrate remnants, such as amino acids and peptides produced from proteolysis of the substrate protein, and biological endpoints of the pathway.

Determining the ability of the ubiquitin protease to bind to a target molecule can also be accomplished using a technology such as real-time Bimolecular Interaction Analysis (BIA). Sjolander et al. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the one-bead one-compound library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer DrugDes.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994)*Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 97:6378–6382); (Felici (1991) *J. Mol. Biol.* 222:301–310); (Ladner supra).

Candidate compounds include, for example, 1) peptides such as soluble peptides, including Ig-tailed fusion peptides and members of random peptide libraries (see, e.g., Lam et al. (1991) *Nature* 354:82–84; Houghten et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length ubiquitin protease or fragment that competes for substrate binding. Other candidate compounds include mutant ubiquitin proteases or appropriate fragments containing mutations that affect ubiquitin protease function and compete for substrate. Accordingly, a fragment that competes for substrate, for example with a higher affinity, or a fragment that binds substrate but does not hydrolyze the peptide bond, is encompassed by the invention.

Other candidate compounds include ubiquitinated protein or protein analog that binds to the protease but is not released or released slowly. Other candidate compounds include analogs of the other natural substrates, such as substrate remnants that bind to but are not released or released more slowly. Further candidate compounds include activators of the proteases such as cytokines, including but not limited to, those disclosed herein.

The invention provides other end points to identify compounds that modulate (stimulate or inhibit) ubiquitin protease activity. The assays typically involve an assay of events in the pathway that indicate ubiquitin protease activity. This can include cellular events that result from deubiquitination, such as cell cycle progression, programmed cell death, growth factor-mediated signal transduction, or any of the cellular processes including, but not limited to, those disclosed herein as resulting from deubiquitination. Specific phenotypes include changes in stress response, DNA replication, receptor internalization, cellular transformation or reversal of transformation, and transcriptional silencing.

Assays are based on the multiple cellular functions of deubiquitinating enzymes. These enzymes act at various different levels in the regulation of protein ubiquitination. A deubiquitinating enzyme can degrade a linear polyubiquitin chain into monomeric ubiquitin molecules. Deubiquitinating enzymes, such as isopeptidase-T, can degrade a branched multiubiquitin chain into monomeric ubiquitin molecules. Deubiquitinating enzymes can remove ubiquitin from a ubiquitin-conjugated target protein. The deubiquitinating enzyme, such as FAF or PA700 isopeptidase, can remove polyubiquitin from a ubiquitinated target protein, and thereby rescue the target from degradation by the 26S proteasome. Deubiquitinating enzymes such as Doa-4 can remove polyubiquitin from proteasome degradation products. UCH family members tend to hydrolyze monoubiquitinated substrate (Larsen et al. (1998) *Biochemistry* 10:3358–68). The UCH deubiquitinating enzyme AP-UCH enhances proteolytic activity of Protein Kinase A (PKA) through the ubiquitin-proteosome pathway. Furthermore, BAP1 has been identified as a new member of the UCH family and interacts with BRAC1, thereby enhancing BRCA1 mediated cell growth suppression (Jensen et al. (1998) *Oncogene* 1,6: 1097–1112). The end result of all of the deubiquitinating enzymes is to regulate the cellular pool of free monomeric ubiquitin. Accordingly, assays can be based on detection of any of the products produced by hydrolysis/deubiquitination.

Further, the expression of genes that are up- or down-regulated by action of the ubiquitin protease can be assayed. In one embodiment, the regulatory region of such genes can be operably linked to a marker that is easily detectable, such as luciferase.

Accordingly, any of the biological or biochemical functions mediated by the ubiquitin protease can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric ubiquitin protease proteins in which one or more domains, sites, and the like, as disclosed herein, or parts thereof, can be replaced by their heterologous counterparts derived from other ubiquitin proteases. For example, a recognition or binding region can be used that interacts with different substrate specificity and/or affinity than the native ubiquitin protease. Accordingly, a different set of pathway components is available as an end-point assay for activation. Further, sites that are responsible for developmental, temporal, or tissue specificity can be replaced by heterologous sites such that the protease can be detected under conditions of specific developmental, temporal, or tissue-specific expression.

The ubiquitin protease polypeptides are also useful in competition binding assays in methods designed to discover compounds that interact with the ubiquitin protease. Thus, a compound is exposed to a ubiquitin protease polypeptide under conditions that allow the compound to bind to or to otherwise interact with the polypeptide. Soluble ubiquitin protease polypeptide is also added to the mixture. If the test compound interacts with the soluble ubiquitin protease polypeptide, it decreases the amount of complex formed or activity from the ubiquitin protease target. This type of assay is particularly useful in cases in which compounds are sought that interact with specific regions of the ubiquitin protease. Thus, the soluble polypeptide that competes with the target ubiquitin protease region is designed to contain peptide sequences corresponding to the region of interest.

Another type of competition-binding assay can be used to discover compounds that interact with specific functional sites. As an example, ubiquitin and a candidate compound can be added to a sample of the ubiquitin protease. Compounds that interact with the ubiquitin protease at the same site as ubiquitin will reduce the amount of complex formed between the ubiquitin protease and ubiquitin. Accordingly, it is possible to discover a compound that specifically prevents interaction between the ubiquitin protease and ubiquitin. Another example involves adding a candidate compound to a sample of ubiquitin protease and polyubiquitin. A compound that competes with polyubiquitin will reduce the amount of hydrolysis or binding of the polyubiquitin to the ubiquitin protease. Accordingly, compounds can be discovered that directly interact with the ubiquitin protease and compete with polyubiquitin. Such assays can involve any other component that interacts with the ubiquitin protease, such as ubiquitinated substrate protein, ubiquitinated substrate remnants, and cellular components with which the protease interacts such as transcriptional regulatory factors.

To perform cell free drug screening assays, it is desirable to immobilize either the ubiquitin protease, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/ubiquitin protease fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of ubiquitin protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a ubiquitin protease-binding target component, such as ubiquitin, polyubiquitin, ubiquitinated substrate protein, ubiquitinated substrate protein remnant, or ubiquitinated remnant amino acid, and a candidate compound are incubated in the ubiquitin protease-presenting wells and the amount of complex trapped in the well can be quantitated. Methods for detecting such complexes, in addition to those described above for the GST-immobilized complexes, include immunodetection of complexes using antibodies reactive with the ubiquitin protease target molecule, or which are reactive with ubiquitin protease and compete With the target molecule; as well as enzyme-linked assays which rely on detecting an enzymatic activity associated with the target molecule.

Modulators of ubiquitin protease activity identified according to these drug screening assays can be used to treat a subject with a disorder mediated or affected by the ubiquitin protease pathway, by treating cells that express the ubiquitin protease or cells in which protease expression is desirable (such as virus-infected cells). Such cells include, for example, fetal kidney, testes, fetal liver, ovary, fetal heart, kidney, thyroid, undifferentiated osteoblasts, skeletal muscle, and malignant breast, lung and colon tissue, as well as liver metastases derived from malignant colonic tissue. These methods of treatment include the steps of administering the modulators of ubiquitin protease activity in a pharmaceutical composition as described herein, to a subject in need of such treatment.

Tissues and/or cells in which the ubiquitin protease is expressed include, but are not limited to those shown in FIGS. 5 and 6. Tissues in which the gene is highly expressed include fetal kidney, testes, fetal liver, ovary, and fetal heart. Expression is also seen in the kidney, thyroid, undifferentiated osteoblasts and skeletal muscle. The ubiquitin protease is also expressed in normal liver and in normal and malignant breast, lung, and colon tissue and in liver metastases derived from malignant colonic tissues. Hence, the ubiquitin protease is relevant to treating disorders involving these tissues, breast, lung, colon carcinoma, and colon metastases to liver.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatter liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such, as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney and nephronophthisis-uremic medullary cystic disease complex, acquired (dialysis-associated) cystic disease and simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schonlein purpura, bacterial endocarditis, diabetic glomerulosclerosis, amyloidosis, fibrillary and immunotactoid glomerulonephritis, and other systemic disorders; diseases affecting tubules and interstitium, including, but not limited to, acute tubular necrosis and tubulointerstitial nephritis, including but not limited to, pyelonephritis and urinary tract infection, acute pyelonephritis, chronic pyelonephritis and reflux nephropathy, tubulointerstitial nephritis induced by drugs and toxins, including but not limited to, acute drug-induced interstitial nephritis, analgesic abuse nephropathy, and nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including, including but not limited to, benign nephrosclerosis, malignant hypertension and accelerated nephrosclerosis, renal artery stenosis, and thrombotic microangiopathies, including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders of the breast include, but are not limited to, disorders of development; inflammations, including but not limited to, acute mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors, such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor, choriocarcinoma, teratoma, and mixed tumors, tumors of sex cord-gonadal stroma including, but not limited to, Leydig (interstitial) cell tumors and Sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors, such as rhabdomyosarcoma.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffiuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporois, paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, ewing saracoma, primitive neuroectodermal tumor, giant cell tumor, and metastatic tumors.

The ubiquitin-proteasome pathway has been implicated in the regulation of viral infection. Recent studies have shown that ubiquitination of the herpes simplex virus type 1 (HSV-1) transactivator protein ICP0 and the hepatitis B virus X protein (HBX) are influenced by the ubiquitin-proteasome pathway during viral infection (Weber et al. (1999) *Virology* 253:288–98 and Hu et al. (1999) *J Virol* 73:7231–40). In addition, inactivation of the ubiquitin-proteasome pathway inhibits Vmw110, an immediate early protein of HSV-1, from stimulating lytic infection. (Everett et al. (1998) *EMBO J* 17:7161–9). Furthermore, a cellular deubiquitinating enzyme, Herpes-virus associated ubiquitin specific protease, HAUSP, has also been implicated in the regulation of HSV infection (Everett et al. (1997) *EMBO J*. 16:1519–1530). Hence, the ubiquitin protease find use in the treatment of disorders resulting from viral infection.

Transcriptional profiling and Taqman profiling techniques showed that the expression of the ubiquitin protease of the present invention was upregulated in HSV-infected human ganglia cells compared to uninfected ganglia. Furthermore, cell lines that express a hepatitis B virus (HepG2.215) showed higher expression levels of the ubiquitin protease 23484 when compared to the parental HepG2 control cell line. The ubiquitin protease 23484 is therefore an important host gene for HSV and HVB pathogenesis and finds use in the treatment of disorders resulting from herpes simplex virus and hepatitis B infection.

Additional disorders in which the ubiquitin protease expression is relevant include, but are not limited to the following:

Respiratory viral pathogens and their associated disorders include, for example, adenovirus, resulting in upper and lower respiratory tract infections; conjuctivitis and diarrhea; echovirus, resulting in upper respiratory tract infections, pharyngitis and rash; rhinovirus, resulting in upper respiratory tract infections; cosackievirus, resulting in Pleurodynia, herpangia, hand-foot-mouth disease; coronavirus, resulting in upper respiratory tract infections; influenza A and B viruses, resulting in influenza; parainfluenza virus 1–4, resulting in upper and lower respiratory tract infections and croup; respiratory syncytial virus, resulting in bronchiolitis and pneumonia.

Digestive viral pathogens and their associated disorders include, for example, mumps virus, resulting in mumps, pancreatitis, and orchitis; rotavirus, resulting in childhood diarrhea; Norwalk Agent, resulting in gastroenteritis; hepatitis A virus, resulting in acute viral hepatitis; hepatitis B virus, hepatitis D virus and hepatitis C virus, resulting in acute or chronic hepatitis; hepatitis E virus, resulting in enterically transmitted hepatitis.

Systemic viral pathogens associated with disorders involving skin eruptions include, for example, measles virus, resulting in measles (rubeola); rubella virus, resulting in German measles (rubella); parvovirus, resulting in erythema infectiosum and aplastic anemia; varicella-zoster virus, resulting in chicken pox and shingles; herpes simplex virus 1-associated, resulting in cold sores; and herpes simplex virus 2, resulting in genital herpes.

Systemic viral pathogens associated with hematopoietic disorders include, for example, cytomegalovirus, resulting in cytomegalic inclusion disease; Epstein-Barr virus, resulting in mononucleosis; HTLV-1, resulting in adult T-cell leukemia and tropical spastic paraparesis; HTLV-II; and HIV 1 and HIV 2, resulting in AIDS.

Arboviral pathogens associated with hemorrhagic fevers include, for example, dengue virus 1–4, resulting in dengue and hemorrhagic fever; yellow fever virus, resulting in yellow fever; Colorado tick fever virus, resulting in Colorado tick fever; and regional hemorrhagic fever viruses, resulting in Bolivian, Argentinian, Lassa fever.

Viral pathogens associated with warty growths and other hyperplasias include, for example, papillomavirus, resulting in condyloma and cervical carcinoma; and molluscum virus, resulting in molluscum contagiosum.

Viral pathogens associated with central nervous system disorders include, for example, poliovirus, resulting in poliomyelitis; rabiesvirus, associated with rabies; JC virus, associated with progressive multifocal leukoencephalopathy; and arboviral encephalitis viruses, resulting in Eastern, Western, Venezuelan, St. Louis, or California group encephalitis.

Viral pathogens associated with cancer include, for example, human papillomaviruses, implicated in the genesis of several cancers including squamous cell carcinoma of the cervix and anogenital region, oral cancer and laryngeal cancers; Epstein-Barr virus, implicated in pathogenesis of the African form of Burkitt lymphoma, B-cell lymphomas, Hodgkin disease, and nasopharyngeal carcinomas; hepatitis B virus, implicated in liver cancer; human T-cell leukemia virus type 1 (HTLV-1), associated with T-cell leukemia/lymphoma; and the Kaposi sarcoma herpesvirus (KSHV).

The ubiquitin protease polypeptides are thus useful for treating a ubiquitin protease-associated disorder characterized by aberrant expression or activity of a ubiquitin protease. The polypeptides can also be useful for treating a disorder characterized by excessive amounts of polyubiquitin or ubiquitinated substrate/remnant/amino acid. In one embodiment, the method involves administering an agent (e.g., an agent identified by a screening assay described herein), or combination of agents that modulates (e.g., upregulates or downregulates) expression or activity of the protein. In another embodiment, the method involves administering the ubiquitin protease as therapy to compensate for reduced or aberrant expression or activity of the protein.

Methods for treatment include but are not limited to the use of soluble ubiquitin protease or fragments of the ubiquitin protease protein that compete for substrates including those disclosed herein. These ubiquitin proteases or fragments can have a higher affinity for the target so as to provide effective competition.

Stimulation of activity is desirable in situations in which the protein is abnormally downregulated and/or in which increased activity is likely to have a beneficial effect, such as virally-infected cells. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer) or a disorder characterized by an aberrant hematopoietic response. In another example, it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283, 317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins (captured proteins) which bind to or interact with the proteins of the invention and modulate their activity.

The ubiquitin protease polypeptides also are useful to provide a target for diagnosing a disease or predisposition to disease mediated by the ubiquitin protease, including, but not limited to, diseases involving tissues in which the ubiquitin proteases are expressed as disclosed herein, such as breast, lung, and liver cancer (colon metastases).

Accordingly, methods are provided for detecting the presence, or levels of, the ubiquitin protease in a cell, tissue, or organism. The method involves contacting a biological sample with a compound capable of interacting with the ubiquitin protease such that the interaction can be detected.

The polypeptides are also useful for treating a disorder characterized by reduced amounts of these components. Thus, increasing or decreasing the activity of the protease is beneficial to treatment. The polypeptides are also useful to provide target for diagnosing a disease characterized by excessive substrate or reduced levels of substrate. Accordingly, where substrate is excessive, use of the protease polypeptides can provide a diagnostic assay. Furthermore, for example, proteases having reduced activity can be used to diagnose conditions in which reduced substrate is responsible for the disorder.

One agent for detecting ubiquitin protease is an antibody capable of selectively binding to ubiquitin protease. A biological sample includes tissues, cells and biological fluids isolated from a subject, as well as tissues, cells and fluids present within a subject.

The ubiquitin protease also provides a target for diagnosing active disease, or predisposition to disease, in a patient having a variant ubiquitin protease. Thus, ubiquitin protease can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered ubiquitin protease activity in cell-based or cell-free assay, alteration in binding to or hydrolysis of polyubiquitin, binding to ubiquitinated substrate protein or hydrolysis of the ubiquitin from the protein, binding to ubiquitinated protein remnant, including peptide or amino acid, and hydrolysis of the ubiquitin from the remnant, general protein turnover, specific protein turnover, antibody-binding pattern, altered isoelectric point, direct amino acid sequencing, and any other of the known assay techniques useful for detecting mutations in a protein in general or in a ubiquitin protease specifically, including assays discussed herein.

In vitro techniques for detection of ubiquitin protease include enzyme linked immunosorbent assays (ELISAs), Western blots, immunoprecipitations and immunofluorescence. Alternatively, the protein can be detected in vivo in a subject by introducing into the subject a labeled anti-ubiquitin protease antibody. For example, the antibody can be labeled with a radioactive marker whose presence and location in a subject can be detected by standard imaging techniques. Particularly useful are methods, which detect the allelic variant of the ubiquitin protease expressed in a subject, and methods, which detect fragments of the ubiquitin protease in a sample.

The ubiquitin protease polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) *Clin. Exp. Pharmacol. Physiol.* 23(10–11):983–985, and Linder, M. W. (1997) *Clin. Chem.* 43(2):254–266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound.

Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the ubiquitim protease in which one or more of the ubiquitin protease functions in one population is different from those in another population. The polypeptides thus allow a target to ascertain a genetic predisposition that can affect treatment modality. Thus, in a ubiquitin-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The ubiquitin protease polypeptides are also useful for monitoring therapeutic effects during clinical trials and other treatment. Thus, the therapeutic effectiveness of an agent that is designed to increase or decrease gene expression, protein levels or ubiquitin protease activity can be monitored over the course of treatment using the ubiquitin protease polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the ubiquitin protease and its variants and fragments. An antibody is considered to selectively bind, even if it also binds to other proteins that are not substantially homologous with the ubiquitin protease. These other proteins share homology with a fragment or domain of the ubiquitin protease. This conservation in specific regions gives rise to antibodies that bind to both proteins by virtue of the homologous sequence. In this case, it would be understood that antibody binding to the ubiquitin protease is still selective.

To generate antibodies, an isolated ubiquitin protease polypeptide is used as an immunogen to generate antibodies using standard techniques for polyclonal and monoclonal antibody preparation. Either the full-length protein or antigenic peptide fragment can be used. Regions having a high antigenicity index are shown in FIG. 2.

Antibodies are preferably prepared from these regions or from discrete fragments in these regions. However, antibodies can be prepared from any region of the peptide as described herein. A preferred fragment produces an antibody that diminishes or completely prevents substrate hydrolysis or binding. Antibodies can be developed against the entire ubiquitin protease or domains of the ubiquitin protease as described herein. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H An appropriate immunogenic preparation can be derived from native, recombinantly expressed, or chemically synthesized peptides.

Antibody Uses

The antibodies can be used to isolate a ubiquitin protease by standard techniques, such as affinity chromatography or immunoprecipitation. The antibodies can facilitate the purification of the natural ubiquitin protease from cells and recombinantly produced ubiquitin protease expressed in host cells.

The antibodies are useful to detect the presence of ubiquitin protease in cells or tissues to determine the pattern of expression of the ubiquitin protease among various tissues in an organism and over the course of normal development.

The antibodies can be used to detect ubiquitin protease in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length ubiquitin protease can be used to identify ubiquitin protease turnover.

Further, the antibodies can be used to assess ubiquitin protease expression in disease states such as in active stages of the disease or in an individual with a predisposition toward disease related to ubiquitin or ubiquitin protease function. When a disorder is caused by an inappropriate tissue distribution, developmental expression, or level of expression of the ubiquitin protease protein, the antibody can be prepared against the normal ubiquitin protease protein. If a disorder is characterized by a specific mutation in the ubiquitin protease, antibodies specific for this mutant protein can be used to assay for the presence of the specific mutant ubiquitin protease. However, intracellularly-made antibodies ("intrabodies") are also encompassed, which would recognize intracellular ubiquitin protease peptide regions.

The antibodies can also be used to assess normal and aberrant subcellular localization of cells in the various tissues in an organism. Antibodies can be developed against the whole ubiquitin protease or portions of the ubiquitin protease.

The diagnostic uses can be applied, not only in genetic testing, but also in monitoring a treatment modality. Accordingly, where treatment is ultimately aimed al correcting ubiquitin protease expression level or the presence of aberrant ubiquitin proteases and aberrant tissue distribution or developmental expression, antibodies directed against the ubiquitin protease or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic ubiquitin protease can be used to identify individuals that require modified treatment modalities.

The antibodies are also useful as diagnostic tools as an immunological marker for aberrant ubiquitin protease analyzed by electrophoretic mobility, isoelectric point, tryptic peptide digest, and other physical assays known to those in the art.

The antibodies are also useful for tissue typing. Thus, where a specific ubiquitin protease has been correlated with expression in a specific tissue, antibodies that are specific for this ubiquitin protease can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting ubiquitin protease function, for example, blocking ubiquitin or polyubiquitin binding, or binding to ubiquitinated substrate or substrate remnants.

These uses can also be applied in a therapeutic context in which treatment involves inhibiting ubiquitin protease function. An antibody can be used, for example, to block ubiquitin binding. Antibodies can be prepared against specific fragments containing sites required for function or against intact ubiquitin protease associated with a cell.

Completely human antibodies are particularly desirable for therapeutic treatment of human patients. For an overview of this technology for producing human antibodies, see Lonberg et al. (1995) *Int. Rev. Immunol.* 13:65–93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of a ubiquitin protease protein in a biological sample. The kit can comprise antibodies such as a labeled or labelable antibody and a compound or agent for detecting ubiquitin protease in a biological sample; means for determining the amount of ubiquitin protease in the sample; and means for comparing the amount of ubiquitin protease in the sample with a standard. The compound or agent can be packaged in a suitable container. The kit can further comprise instructions for using the kit to detect ubiquitin protease.

Polynucleotides

The nucleotide sequence in SEQ ID NO 2 was obtained by sequencing the deposited human cDNA. Accordingly, the sequence of the deposited clone is controlling as to any discrepancies between the two and any reference to the sequence of SEQ ID NO 2 includes reference to the sequence of the deposited cDNA.

The specifically disclosed cDNA comprises the coding region and 5' and 3' untranslated sequences in SEQ ID NO 2.

The invention provides isolated polynucleotides encoding the novel ubiquitin protease. The term "ubiquitin protease polynucleotide" or "ubiquitin protease nucleic acid" refers to the sequence shown in SEQ ID NO 2 or in the deposited cDNA. The term "ubiquitin protease polynucleotide" or "ubiquitin protease nucleic acid" further includes variants and fragments of the ubiquitin protease polynucleotide.

An "isolated" ubiquitin protease nucleic acid is one that is separated from other nucleic acid present in the natural source of the ubiquitin protease nucleic acid. Preferably, an "isolated" nucleic acid is free of sequences which naturally flank the ubiquitin protease nucleic acid (i.e., sequences located at the 5' and 3' ends of the nucleic acid) in the genomic DNA of the organism from which the nucleic acid is derived. However, there can be some flanking nucleotide sequences, for example up to about 5KB. The important point is that the ubiquitin protease nucleic acid is isolated from flanking sequences such that it can be subjected to the specific manipulations described herein, such as recombinant expression, preparation of probes and primers, and other uses specific to the ubiquitin protease nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as BPLC. Preferably, an isolated nucleic acid comprises at least about 50, 80 or 90% (on a molar basis) of all macromolecular species present.

The ubiquitin protease polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The ubiquitin protease polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Ubiquitin protease polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

Ubiquitin protease nucleic acid can comprise the nucleotide sequence shown in SEQ ID NO 2, corresponding to human cDNA.

In one embodiment, the ubiquitin protease nucleic acid comprises only the coding region.

The invention further provides variant ubiquitin protease polynucleotides, and fragments thereof, that differ from the nucleotide sequence shown in SEQ ID NO 2 due to degeneracy of the genetic code and thus encode the same protein as that encoded by the nucleotide sequence shown in SEQ ID NO 2.

The invention also provides ubiquitin protease nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecule of SEQ ID NO 2 and the complements thereof Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a ubiquitin protease that is at least about 60–65%, 65–70%, typically at least about 70–75%, more typically at least about 80–85%, and most typically at least about 90–95% or more homologous to the nucleotide sequence shown in SEQ ID NO 2. Such nucleic acid molecules can readily be identified as being able to hybridize under stringent conditions, to the nucleotide sequence shown in SEQ ID NO 2 or a fragment of the sequence. It is understood that stringent hybridization does not indicate substantial homology where it is due to general homology, such as poly A sequences, or sequences common to all or most proteins or all deubiquitinating enzymes. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 60–65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in Current Protocols in Molecular Biology, John Wiley & Sons, New York (1989), 6.3.1–6.3.6, incorporated by reference. One example of stringent hybridization conditions are hybridization in 6× sodium chloridelsodium citrate (SSC) at about 45° C., followed by one or more washes in 0.2×SSC, 0.1% SDS at 50–65° C. In another non-limiting example, nucleic acid molecules are allowed to hybridize in 6× sodium chloride/sodium citrate (SSC) at about 45° C., followed by one or more low stringency washes in 0.2×SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO 1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO 2 or the complement of SEQ ID NO 2. In one embodiment, the nucleic acid consists of a portion of the nucleotide sequence of SEQ ID NO 2 or the complement of SEQ ID NO 2.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 15, preferably at least about 18, 20, 23 or 25 nucleotides, and can be 30, 40, 50, 100, 200, 500 or more nucleotides in length.

For example, nucleotide sequences 1 to about 269, about 761 to about 817, about 994 to about 1554, and about 1735 to about 2314 are not disclosed prior to the invention. The nucleotide sequence from about 269 to 761 encompasses fragments greater than 14, 18, 20, 23 or 25 nucleotides; the nucleotide sequence from about 817 to about 994 encompasses fragments greater than 6, 10, 15, 20, or 25 nucleotides; the nucleotide sequences from about 1154 to 1735 encompasses fragments greater than 13, 18, 20, 23 or 25 nucleotides; and the nucleotide sequence from about 2314 to about 2520 encompasses fragments greater than 33, 40, 45, or 50 nucleotides. Longer fragments, for example, 30 or more nucleotides in length, which encode antigenic proteins or polypeptides described herein are useful, Furthermore, the invention provides polynucleotides that comprise a fragment of the full-length ubiquitin protease polynucleotides. The fragment can be single or double-stranded and can comprise DNA or RNA. The fragment can be derived from either the coding or the non-coding sequence.

In another embodiment an isolated ubiquitin protease nucleic acid encodes the entire coding region. Other fragments include nucleotide sequences encoding the amino acid fragments described herein.

Thus, ubiquitin protease nucleic acid fragments further include sequences corresponding to the domains described herein, subregions also described, and specific functional sites. Ubiquitin protease nucleic acid fragments also include combinations of the domains, segments, and other functional sites described above. A person of ordinary skill in the art would be aware of the many permutations that are possible.

Where the location of the domains or sites have been predicted by computer analysis, one of ordinary sill would appreciate that the amino acid residues constituting these domains can vary depending on the criteria used to define the domains.

However, it is understood that a ubiquitin protease fragment includes any nucleic acid sequence that does not include the entire gene.

The invention also provides ubiquitin protease nucleic acid fragments that encode epitope bearing regions of the ubiquitin protease proteins described herein.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) J. Mol. Biol. 215:403–10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) Nucleic Acids Res. 25(17):3389–3402. When utilizing BLAST and Gapped BLAST programs, the default parameters of the respective programs (e.g., XBLAST and NBLAST) can be used.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen el al. (1991) Science 254:1497–1500. Typically, a probe comprises a region of nucleotide sequence that hybridizes under highly stringent conditions to at least about 15, typically about 20–25, and more typically about 40, 50 or 75 consecutive nucleotides of the nucleic acid sequence shown in SEQ ID NO 2 and the complements thereof More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using wellknown methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The ubiquitin protease polynucleotides are thus useful for probes, primers, and in biological assays.

Where the polynucleotides are used to assess ubiquitin protease properties or functions, such as in the assays described herein, all or less than all of the entire cDNA can be useful. Assays specifically directed to ubiquitin protease functions, such as assessing agonist or antagonist activity, encompass the use of known fragments. Further, diagnostic methods for assessing ubiquitin protease function can also be practiced with any fragment, including those fragments that may have been known prior to the invention. Similarly, in methods involving treatment of ubiquitin protease dysfunction, all fragments are encompassed including those, which may have been known in the art.

The ubiquitin protease polynucleotides are usefl as a hybridization probe for cDNA and genomic DNA to isolate a full-length cDNA and genomic clones encoding the polypeptide described in SEQ ID NO 1 and to isolate cDNA and genomic clones that correspond to variants producing the same polypeptide shown in SEQ ID NO 1 or the other variants described herein. Variants can be isolated from the same tissue and organism from which the polypeptides shown in SEQ ID NO 1 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the ubiquitin protease. Accordingly, it could be derived from 5' noncoding regions, the coding region, and 3' noncoding regions.

The nucleic acid probe can be, for example, the full-length cDNA of SEQ ID NO 2 or a fragment thereof that is sufficient to specifically hybridize under stringent conditions to MRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also usefull to synthesize antisense molecules of desired length and sequence.

Antisense nucleic acids of the invention can be designed using the nucleotide sequence of SEQ ID NO 2, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357–63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell ubiquitin proteases in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm Res.* 5:539–549).

The ubiquitin protease polynucleotides are also useful as primers for PCR to amplify any given region of a ubiquitin protease polynucleotide.

The ubiquitin protease polynucleotides are also useful for constructing recombinant vectors. Such vectors include expression vectors that express a portion of, or all of, the ubiquitin protease polypeptides. Vectors also include insertion vectors, used to integrate into another polynucleotide sequence, such as into the cellular genome, to alter in situ expression of ubiquitin protease genes and gene products. For example, an endogenous ubiquitin protease coding sequence can be replaced via homologous recombination with all or part of the coding region containing one or more specifically introduced mutations.

The ubiquitin protease polynucleotides are also useful for expressing antigenic portions of the ubiquitin protease proteins.

The ubiquitin protease polynucleotides are also useful as probes for determining the chromosomal positions of the ubiquitin protease polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland el al. ((1987) *Nature* 325:783–787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The ubiquitin protease polynucleotide probes are also useful to determine patterns of the presence of the gene encoding the ubiquitin proteases and their variants with respect to tissue distribution, for example, whether gene duplication has occurred and whether the duplication occurs in all or only a subset of tissues. The genes can be naturally occurring or can have been introduced into a cell, tissue, or organism exogenously.

The ubiquitin protease polynucleotides are also useful for designing ribozymes corresponding to all, or a part, of the mRNA produced from genes encoding the polynucleotides described herein.

The ubiquitin protease polynucleotides are also useful for constructing host cells expressing a part, or all, of the ubiquitin protease polynucleotides and polypeptides.

The ubiquitin protease polynucleotides are also useful for constructing transgenic animals expressing all, or a part, of the ubiquitin protease polynucleotides and polypeptides.

The ubiquitin protease polynucleotides are also useful for making vectors that express part, or all, of the ubiquitin protease polypeptides.

The ubiquitin protease polynucleotides are also useful as hybridization probes for determining the level of ubiquitin protease nucleic acid expression. Accordingly, the probes can be used to detect the presence of, or to determine levels of, ubiquitin protease nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the ubiquitin protease genes.

Alternatively, the probe can be used in an in situ hybridization context to assess the position of extra copies of the ubiquitin protease genes, as on extrachromosomal elements or as integrated into chromosomes in which the ubiquitin protease gene is not normally found, for example as a homogeneously staining region.

These uses are relevant for diagnosis of disorders involving an increase or decrease in ubiquitin protease expression relative to normal, such as a proliferative disorder, a differentiative or developmental disorder, or a hematopoietic disorder.

Tissues and/or cells in which the ubiquitin protease is expressed include, but are not limited to those shown in FIGS. 5 and 6. Tissues in which the gene is highly expressed include fetal kidney, testes, fetal liver, ovary, and fetal heart. Expression is also seen in the kidney, thyroid, undifferentiated osteoblasts and skeletal muscle. The ubiquitin protease is also expressed in normal liver and in normal and malignant breast, lung, and colon tissue and in liver metastases derived from malignant colonic tissues. The ubiquitin proteases are thus specifically involved in breast, lung, and liver cancer.

As such, the gene is particularly relevant for the treatment of disorders involving these tissues. Disorders in which the ubiquitin protease expression is relevant are disclosed herein above.

Furthermore, the ubiquitin protease is useful to treat viral infections and disorders resulting from viral infections. Such disorders are discussed above.

Thus, the present invention provides a method for identifying a disease or disorder associated with aberrant expression or activity of ubiquitin protease nucleic acid, in which a test sample is obtained from a subject and nucleic acid (e.g., MRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the ubiquitin protease, such as by measuring the level of a ubiquitin protease-encoding nucleic acid in a sample of cells from a subject e.g., mRNA or genomic DNA, or determining if the ubiquitin protease gene has been mutated.

Nucleic acid expression assays are useful for drug screening to identify compounds that modulate ubiquitin protease nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the ubiquitin protease gene. The method typically includes assaying the ability of the compound to modulate the expression of the ubiquitin protease nucleic acid and thus identifying a compound that can be used to treat a disorder characterized by undesired ubiquitin protease nucleic acid expression.

The assays can be performed in cell-based and cell-free systems. Cell-based assays include cells naturally expressing the ubiquitin protease nucleic acid or recombinant cells genetically engineered to express specific nucleic acid sequences.

Alternatively, candidate compounds can be assayed in vivo in patients or in transgenic animals.

The assay for ubiquitin protease nucleic acid expression can involve direct assay of nucleic acid levels, such as mRNA levels, or on collateral compounds involved in the pathway (such as free ubiquitin pool or protein turnover). Further, the expression of genes that are up- or down-regulated in response to the ubiquitin protease activity can also be assayed. In this embodiment the regulatory regions of these genes can be operably linked to a reporter gene such as luciferase.

Thus, modulators of ubiquitin protease gene expression can be identified in a method wherein a cell is contacted with a candidate compound and the expression of mRNA determined. The level of expression of ubiquitin protease mRNA in the presence of the candidate compound is compared to the level of expression of ubiquitin protease mRNA in the absence ofthe candidate compound. The candidate compound can then be identified as a modulator of nucleic acid expression based on this comparison and be used, for example to treat a disorder characterized by aberrant nucleic acid expression. When expression of MRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate ubiquitin protease nucleic acid expression. Modulation includes both up-regulation (i.e. activation or agonization) or down-regulation (suppression or antagonization) or effects on nucleic acid activity (e.g. when nucleic acid is mutated or improperly modified). Treatment includes disorders characterized by aberrant expression or activity of the nucleic acid. In addition, disorders that are influenced by the ubiquitin protease may also be treated. Examples of such disorders are disclosed herein.

Alternatively, a modulator for ubiquitin protease nucleic acid expression can be a small molecule or drug identified using the screening assays described herein as long as the drug or small molecule inhibits the ubiquitin protease nucleic acid expression.

The ubiquitin protease polynucleotides are also useful for monitoring the effectiveness of modulating compounds on the expression or activity of the ubiquitin protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the MRNA or genomic DNA in the pre-administration sample with the mRNA or genomic DNA in the post-administration sample or samples; and (vi) increasing or decreasing the administration of the agent to the subject accordingly.

The ubiquitin protease polynucleotides are also useful in diagnostic assays for qualitative changes in ubiquitin protease nucleic acid, and particularly in qualitative changes that lead to pathology. The polynucleotides can be used to detect mutations in ubiquitin protease genes and gene expression products such as mRNA. The polynucleotides can be used as hybridization probes to detect naturally-occurring genetic mutations in the ubiquitin protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the ubiquitin protease gene associated with a dysfunction provides a diagnostic tool for an active disease or susceptibility to disease when the disease results from overexpression, underexpression, or altered expression of a ubiquitin protease.

Mutations in the ubiquitin protease gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364, the latter of which can be particularly useful for detecting point mutations in the gene (see Abravaya et al. (1995) *Nucleic Acids Res.* 23:675–682). This method can include the steps of collecting a sample of cells from a patient, isolating nucleic acid (e.g., genomic, MRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a ubiquitin protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant ubiquitin protease gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton et al. (1993) *Mutat Res.* 285:125–144; and Hayashi et al. (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244–255; Kozal et al. (1996) *Nature Medicine* 2:753–759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The ubiquitin protease polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the ubiquitin protease gene that results in altered affinity for ubiquitin could result in an excessive or decreased drug effect with standard concentrations of ubiquitin or analog. Accordingly, the ubiquitin protease polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of MRNA or genomic DNA in the test sample.

The ubiquitin protease polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The ubiquitin protease polynucleotides can also be used to identify individuals based on small biological samples. This can be done for example using restriction fragment-length polymorphism (RFLP) to identify an individual. Thus, the polynucleotides described herein are useful as DNA markers for RFLP (See U. S. Pat. No. 5,272,057).

Furthermore, the ubiquitin protease sequence can be used to provide an alternative technique, which determines the actual DNA sequence of selected fragments in the genome of an individual. Thus, the ubiquitin protease sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The ubiquitin protease sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The ubiquitin protease polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The ubiquitin protease polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The ubiquitin protease polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of ubiquitin protease probes can be used to identify tissue by species and/or by organ type.

In a similar fashion, these primers and probes can be used to screen tissue culture for contamination (i.e. screen for the presence of a mixture of different types of cells in a culture).

Alternatively, the ubiquitin protease polynucleotides can be used directly to block transcription or translation of ubiquitin protease gene sequences by means of antisense or ribozyme constructs. Thus, in a disorder characterized by abnormally high or undesirable ubiquitin protease gene expression, nucleic acids can be directly used for treatment.

The ubiquitin protease polynucleotides are thus useful as antisense constructs to control ubiquitin protease gene expression in cells, tissues, and organisms. A DNA antisense polynucleotide is designed to be complementary to a region of the gene involved in transcription, preventing transcription and hence production of ubiquitin protease protein. An antisense RNA or DNA polynucleotide would hybridize to the mRNA and thus block translation of MRNA into ubiquitin protease protein.

Examples of antisense molecules useful to inhibit nucleic acid expression include antisense molecules complementary to a fragment of the 5' untranslated region of SEQ ID NO 2 which also includes the start codon and antisense molecules which are complementary to a fragment of the 3' untranslated region of SEQ ID NO 2.

Alternatively, a class of antisense molecules can be used to inactivate mRNA in order to decrease expression of ubiquitin protease nucleic acid. Accordingly, these molecules can treat a disorder characterized by abnormal or undesired ubiquitin protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the ubiquitin protease protein.

The ubiquitin protease polynucleotides also provide vectors for gene therapy in patients containing cells that are aberrant in ubiquitin protease gene expression. Thus, recombinant cells, which include the patient's cells that have been engineered ex vivo and returned to the patient, are introduced into an individual where the cells produce the desired ubiquitin protease protein to treat the individual.

The invention also encompasses kits for detecting the presence of a ubiquitin protease nucleic acid in a biological sample. For example, the kit can comprise reagents such as a labeled or labelable nucleic acid or agent capable of detecting ubiquitin protease nucleic acid in a biological sample; means for determining the amount of ubiquitin protease nucleic acid in the sample; and means for comparing the amount of ubiquitin protease nucleic acid in the sample with a standard. The compound or agent can be packaged in a suitable container. The kit can further comprise instructions for using the kit to detect ubiquitin protease mRNA or DNA.

Computer Readable Means

The nucleotide or amino acid sequences of the invention are also provided in a variety of mediums to facilitate use thereof As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein encoding fragments and are usefull in producing commercially important proteins such as enzymes used in various reactions and in the production of commercially useful metabolites.

Vectors/Host Cells

The invention also provides vectors containing the ubiquitin protease polynucleotides. The term "vector" refers to a vehicle, preferably a nucleic acid molecule that can transport the ubiquitin protease polynucleotides. When the vector is a nucleic acid molecule, the ubiquitin protease polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the ubiquitin protease polynucleotides. Alternatively, the vector may integrate into the host cell genome and produce additional copies of the ubiquitin protease polynucleotides when the host cell replicates.

The invention provides vectors for the maintenance (cloning vectors) or vectors for expression (expression vectors) of the ubiquitin protease polynucleotides. The vectors can function in procaryotic or eukaryotic cells or in both (shuttle vectors).

Expression vectors contain cis-acting regulatory regions that are operably linked in the vector to the ubiquitin protease polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the ubiquitin protease polynucleotides from the vector. Alternatively, a trans-acting factor may be supplied by the host cell. Finally, a trans-acting factor can be produced from the vector itself It is understood, however, that in some embodiments, transcription and/or translation of the ubiquitin protease polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual 2nd ed.*, Cold Spring Harbor Laboratory Press, Cold Spring Harbor, N.Y.).

A variety of expression vectors can be used to express a ubiquitin protease polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual 2nd ed.*, Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The ubiquitin protease polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the polypeptide as a fusion protein. Accordingly, the invention provides fusion vectors that allow for the production of the ubiquitin protease polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301–315) and pET 11d (Studier et al. (1990) *Gene Expression Technology: Methods in Enzymology* 185:60–89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119–128). Alternatively, the sequence of the polynucleotide of interest can be altered to provide preferential codon usage for a specific host cell, for example *E. coli*. (Wada et al. (1992) *Nucleic Acids Res.* 20:2111–2118).

The ubiquitin protease polynucleotides can also be expressed by expression vectors that are operative in yeast. Examples of vectors for expression in yeast e.g., *S. cerevisiae* include pYepSec1 (Baldari et al. (1987) *EMBO J.* 6:229–234), pMFa (Kurjan et al. (1982) *Cell* 30:933–943), pJRY88 (Schultz et al. (1987) *Gene* 54:113–123), and pYES2 (Invitrogen Corporation, San Diego, Calif.).

The ubiquitin protease polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow et al. (1989) *Virology* 170:31–39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187–195).

The expression vectors listed herein are provided by way of example only of the well-known vectors available to those of ordinary skill in the art that would be useful to express the ubiquitin protease polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual 2nd, ed*, Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual*, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the ubiquitin protease polynucleotides can be introduced either alone or with other polynucleotides that are not related to the ubiquitin protease polynucleotides such as those providing trans-acting factors for expression vectors. When more than one vector is introduced into a cell, the vectors can be introduced independently, co-introduced or joined to the ubiquitin protease polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the ubiquitin protease polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing ubiquitin protease proteins or polypeptides that can be further purified to produce desired amounts of ubiquitin protease protein or fragments. Thus, host cells containing expression vectors are useful for polypeptide production.

Host cells are also useful for conducting cell-based assays involving the ubiquitin protease or ubiquitin protease fragments. Thus, a recombinant host cell expressing a native ubiquitin protease is useful to assay for compounds that stimulate or inhibit ubiquitin protease function. This includes disappearance of substrate (polyubiquitin, ubiquitinated substrate protein, ubiquitinated substrate remnants), appearance of end product (ubiquitin monomers, polyubiquitin hydrolyzed from substrate or substrate remnant, free substrate that has been rescued by hydrolysis of ubiquitin), general or specific protein turnover, and the various other molecular functions described herein that include, but are not limited to, substrate recognition, substrate binding, subunit association, and interaction with other cellular components. Modulation of gene expression can occur at the level of transcription or translation.

Host cells are also useful for identifying ubiquitin protease mutants in which these functions are affected. If the mutants naturally occur and give rise to a pathology, host cells containing the mutations are useful to assay compounds that have a desired effect on the mutant ubiquitin protease (for example, stimulating or inhibiting function which may not be indicated by their effect on the native ubiquitin protease.

Recombinant host cells are also useful for expressing the chimeric polypeptides described herein to assess compounds that activate or suppress activation or alter specific function by means of a heterologous domain, segment, site, and the like, as disclosed herein.

Further, mutant ubiquitin proteases can be designed in which one or more of the various functions is engineered to be increased or decreased (e.g., binding to ubiquitin, polyubiquitin, or ubiquitinated protein substrate) and used to augment or replace ubiquitin protease proteins in an individual. Thus, host cells can provide a therapeutic benefit by replacing an aberrant ubiquitin protease or providing an aberrant ubiquitin protease that provides a therapeutic result. In one embodiment, the cells provide ubiquitin proteases that are abnormally active.

In another embodiment, the cells provide ubiquitin proteases that are abnormally inactive. These ubiquitin proteases can compete with endogenous ubiquitin proteases in the individual.

In another embodiment, cells expressing ubiquitin proteases that cannot be activated, are introduced into an individual in order to compete with endogenous ubiquitin proteases for ubiquitin substrates. For example, in the case in which excessive ubiquitin substrate or analog is part of a treatment modality, it may be necessary to inactivate this molecule at a specific point in treatment. Providing cells that compete for the molecule, but which cannot be affected by ubiquitin protease activation would be beneficial.

Homologously recombinant host cells can also be produced that allow the in situ alteration of endogenous ubiquitin protease polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the ubiquitin protease polynucleotides or sequences proximal or distal to a ubiquitin protease gene are allowed to integrate into a host cell genome by homologous recombination where expression of the gene can be affected. In one embodiment, regulatory sequences are introduced that either increase or decrease expression of an endogenous sequence. Accordingly, a ubiquitin protease can be produced in a cell not normally producing it. Alternatively, increased expression of ubiquitin protease can be effected in a cell normally producing the protein at a specific level. Further, expression can be decreased or eliminated by introducing a specific regulatory sequence. The regulatory sequence can be heterologous to the ubiquitin protease protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant ubiquitin protease proteins. Such mutations could be introduced, for example, into the specific functional regions such as the ligand-binding site.

In one embodiment, the host cell can be a fertilized oocyte or embryonic stem cell that can be used to produce a transgenic animal containing the altered ubiquitin protease gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous ubiquitin protease gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a ubiquitin protease protein and identifying and evaluating modulators of ubiquitin protease protein activity.

Other examples of transgenic animals include non-human primates, sheep, dogs, cows, goats, chickens, and amphibians.

In one embodiment, a host cell is a fertilized oocyte or an embryonic stem cell into which ubiquitin protease polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the ubiquitin protease nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the ubiquitin protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ hase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect, for example, binding, activation, and protein turnover, may not be evident from jn vitro cell-free or cell-based assays. Accordingly, it is useful to provide non-human transgenic animals to assay in vivo ubiquitin protease function, including substrate interaction, the effect of specific mutant ubiquitin proteases on ubiquitin protease function and substrate interaction, and the effect of chimeric ubiquitin proteases. It is also possible to assess the effect of null mutations, that is mutations that substantially or completely eliminate one or more ubiquitin protease functions.

In general, methods for producing transgenic animals include introducing a nucleic acid sequence according to the present invention, the nucleic acid sequence capable of expressing the receptor protein in a transgenic animal, into a cell in culture or in vivo. When introduced in vivo, the nucleic acid is introduced into an intact organism such that one or more cell types and, accordingly, one or more tissue types, express the nucleic acid encoding the receptor protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

The ubiquitin protease nucleic acid molecules, protein modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a ubiquitin protease protein or anti-ubiquitin protease antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the purview of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micro grams per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

That which is claimed:

1. An isolated nucleic acid molecule comprising a nucleotide sequence set forth in SEQ ID NO:2.

2. A nucleic acid vector comprising the nucleic acid sequence set forth in claim 1.

3. An isolated host cell comprising the nucleic acid vector of claim 2.

4. The isolated host cell of claim 3, wherein the host cell is a mammalian cell.

5. An isolated host cell comprising the nucleic acid molecule set forth in claim 1 wherein said nucleic acid molecule is operably linked to a heterologous promoter.

6. The host cell of claim 5, wherein said cell is a mammalian host cell.

7. The mammalian host cell of claim 6, wherein the host cell is a non-human mammalian host cell.

8. The nucleic acid molecule of claim 1 further comprising nucleic acid sequences encoding a heterologous polypeptide.

9. An isolated nucleic acid molecule comprising a nucleotide sequence having at least 70% identity to SEQ ID NO:2 and encodes a polypeptide having ubiquitin protease activity.

10. The isolated nucleic acid molecule of claim 9, wherein said sequence comprises a nucleotide sequence having at least 80% identity to SEQ ID NO:2 and encodes a polypeptide having ubiquitin protease activity.

11. The isolated nucleic acid molecule of claim 10, wherein said sequence comprises a nucleotide sequence having at least 90% identity to SEQ ID NO:2 and encodes a polypeptide having ubiquitin protease activity.

12. The isolated nucleic acid molecule of claim 11, wherein said sequence comprises a nucleotide sequence having at least 95% identity to SEQ ID NO:2 and encodes a polypeptide having ubiquitin protease activity.

13. An isolated nucleic acid molecule having the nucleic acid sequence of the cDNA insert of the plasmid deposited with ATCC as Accession Number PTA-1849.

14. An isolated nucleic acid molecule comprising a nucleotide sequence having at least 70% identity to the cDNA insert of the plasmid deposited with ATCC as Accession Number PTA-1849 and said sequence encodes a polypeptide having ubiquitin protease activity.

15. The isolated nucleic acid molecule of claim 14, wherein said sequence comprises a nucleotide sequence having at least 80% identity to the cDNA insert of the plasmid deposited with ATCC as Accession Number PTA-1849 and said sequence encodes a polypeptide having ubiquitin protease activity.

16. The isolated nucleic acid molecule of claim 15, wherein said sequence comprises a nucleotide sequence having at least 90% identity to the cDNA insert of the plasmid deposited with ATCC as Accession Number PTA-1849 and said sequence encodes a polypeptide having ubiquitin protease activity.

17. The isolated nucleic acid molecule of clam 16, wherein said sequence comprises a nucleotide sequence having at least 95% identity to the cDNA insert of the plasmid deposited with ATCC as Accession Number PTA-1849 and said sequence encodes a polypeptide having ubiquitin protease activity.

18. An isolated nucleic acid molecule which encodes a polypeptide comprising the amino acid sequence of SEQ ID NO:1.

* * * * *

UNITED STATES PATENT AND TRADEMARK OFFICE
CERTIFICATE OF CORRECTION

PATENT NO. : 6,329,171 B1
DATED : December 11, 2001
INVENTOR(S) : Kapeller-Libermann It is certified that error appears in the above-identified patent and that said Letters Patent is hereby corrected as shown below:

Column 6,
Lines 13-15, delete ", or as ATCC No. PTA-1849 on May 9, 2000 ("the deposited cDNA")".

Column 74,
Line 43, "clam" should read -- claim --.

Signed and Sealed this

Tenth Day of September, 2002

*Attest:*

*Attesting Officer*

JAMES E. ROGAN
*Director of the United States Patent and Trademark Office*